(12) United States Patent
Milne et al.

(10) Patent No.: US 11,642,042 B2
(45) Date of Patent: *May 9, 2023

(54) SYSTEMS AND METHODS FOR MISSED BREATH DETECTION AND INDICATION

(71) Applicant: Covidien LP, Mansfield, MA (US)

(72) Inventors: Gary Milne, Louisville, CO (US); David Hyde, Oceanside, CA (US)

(73) Assignee: Covidien LP, Mansfield, MA (US)

( * ) Notice: Subject to any disclaimer, the term of this patent is extended or adjusted under 35 U.S.C. 154(b) by 1011 days.

This patent is subject to a terminal disclaimer.

(21) Appl. No.: 16/424,806

(22) Filed: May 29, 2019

(65) Prior Publication Data

US 2019/0274585 A1     Sep. 12, 2019

Related U.S. Application Data

(63) Continuation of application No. 13/544,462, filed on Jul. 9, 2012, now Pat. No. 10,362,967.

(51) Int. Cl.
  *A61B 5/08*   (2006.01)
  *A61M 16/00*  (2006.01)
  *A61B 5/087*  (2006.01)

(52) U.S. Cl.
  CPC ....... *A61B 5/0816* (2013.01); *A61M 16/0051* (2013.01); *A61M 16/024* (2017.08); *A61B 5/087* (2013.01); *A61B 5/0826* (2013.01); *A61M 16/0063* (2014.02); *A61M 2016/0021* (2013.01); *A61M 2016/0027* (2013.01); *A61M 2016/0033* (2013.01); *A61M 2205/505* (2013.01); *A61M 2205/52* (2013.01)

(58) Field of Classification Search
  CPC ...... A61B 5/0816; A61B 5/0826; A61B 5/087
  See application file for complete search history.

(56) References Cited

U.S. PATENT DOCUMENTS

| | | |
|---|---|---|
| 1,202,125 A | 10/1916 | Tullar |
| 1,202,126 A | 10/1916 | Tullar |
| 1,241,056 A | 9/1917 | Tullar |
| 2,914,067 A | 11/1959 | Meidenbauer |
| 3,339,545 A | 9/1967 | Barnett |
| 3,575,167 A | 4/1971 | Michielsen |
| 3,577,984 A | 5/1971 | Levy et al. |
| 3,584,618 A | 6/1971 | Reinhard et al. |
| 3,628,531 A | 12/1971 | Harris |

(Continued)

FOREIGN PATENT DOCUMENTS

| | | |
|---|---|---|
| EP | 0414777 | 3/1991 |
| EP | 521515  | 1/1993 |

(Continued)

OTHER PUBLICATIONS

US 7,284,551 B2, 10/2007, Jones et al. (withdrawn)

(Continued)

*Primary Examiner* — Puya Agahi

(57) ABSTRACT

This disclosure describes improved systems and methods for displaying respiratory data to a clinician in a ventilatory system. Respiratory data may be displayed by any number of suitable means, for example, via appropriate graphs, diagrams, charts, waveforms, and other graphic displays. The disclosure describes novel systems and methods for determining and displaying ineffective patient inspiratory or expiratory efforts or missed breaths in a manner easily deciphered by a clinician.

14 Claims, 6 Drawing Sheets

(56) References Cited

U.S. PATENT DOCUMENTS

| | | |
|---|---|---|
| 3,643,652 A | 2/1972 | Beltran |
| 3,659,590 A | 5/1972 | Jones et al. |
| 3,677,267 A | 7/1972 | Richards |
| 3,722,510 A | 3/1973 | Parker |
| 3,739,776 A | 6/1973 | Bird et al. |
| 3,759,249 A | 9/1973 | Fletcher et al. |
| 3,871,371 A | 3/1975 | Weigl |
| 3,908,704 A | 9/1975 | Clement et al. |
| 3,911,899 A | 10/1975 | Hattes |
| 3,940,742 A | 2/1976 | Hudspeth et al. |
| 3,952,739 A | 4/1976 | Cibulka |
| 3,957,044 A | 5/1976 | Fletcher et al. |
| 3,961,624 A | 6/1976 | Weigl |
| 3,961,627 A | 6/1976 | Ernst et al. |
| 3,968,794 A | 7/1976 | O'Neill |
| 3,968,795 A | 7/1976 | O'Neill et al. |
| 3,977,394 A | 8/1976 | Jones et al. |
| 3,985,131 A | 10/1976 | Buck et al. |
| 3,991,304 A | 11/1976 | Hillsman |
| 3,996,928 A | 12/1976 | Marx |
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,095,592 A | 6/1978 | Delphia |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,281,651 A | 8/1981 | Cox |
| 4,284,075 A | 8/1981 | Krasberg |
| 4,294,242 A | 10/1981 | Cowans |
| 4,296,756 A | 10/1981 | Dunning et al. |
| 4,299,236 A | 11/1981 | Poirier |
| 4,308,872 A | 1/1982 | Watson et al. |
| 4,316,182 A | 2/1982 | Hodgson |
| 4,323,064 A | 4/1982 | Hoenig et al. |
| 4,326,513 A | 4/1982 | Schulz et al. |
| 4,366,821 A | 1/1983 | Wittmaier et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,421,113 A | 12/1983 | Gedeon et al. |
| 4,433,693 A | 2/1984 | Hochstein |
| 4,440,166 A | 4/1984 | Winkler et al. |
| 4,440,177 A | 4/1984 | Anderson et al. |
| 4,442,835 A | 4/1984 | Carnegie |
| 4,444,201 A | 4/1984 | Itoh |
| 4,459,982 A | 7/1984 | Fry |
| 4,463,764 A | 8/1984 | Anderson et al. |
| 4,473,081 A | 9/1984 | Dioguardi et al. |
| 4,495,944 A | 1/1985 | Brisson et al. |
| 4,498,471 A | 2/1985 | Kranz et al. |
| 4,503,850 A | 3/1985 | Pasternak |
| 4,506,667 A | 3/1985 | Ansite |
| 4,522,639 A | 6/1985 | Ansite et al. |
| 4,537,190 A | 8/1985 | Caillot et al. |
| 4,550,726 A | 11/1985 | McEwen |
| 4,579,115 A | 4/1986 | Wallroth et al. |
| 4,606,340 A | 8/1986 | Ansite |
| 4,630,605 A | 12/1986 | Pasternack |
| 4,637,385 A | 1/1987 | Rusz |
| 4,648,407 A | 3/1987 | Sackner |
| 4,653,493 A | 3/1987 | Hoppough |
| 4,654,029 A | 3/1987 | D'Antonio |
| 4,702,240 A | 10/1987 | Chaoui |
| 4,721,060 A | 1/1988 | Cannon et al. |
| 4,736,750 A | 4/1988 | Valdespino et al. |
| 4,752,089 A | 6/1988 | Carter |
| 4,790,327 A | 12/1988 | Despotis |
| 4,790,832 A | 12/1988 | Lopez |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,870,960 A | 10/1989 | Hradek |
| 4,870,961 A | 10/1989 | Barnard |
| 4,876,903 A | 10/1989 | Budinger |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,016,626 A | 5/1991 | Jones |
| 5,020,527 A | 6/1991 | Dessertine |
| 5,021,046 A | 6/1991 | Wallace |
| 5,022,393 A | 6/1991 | McGrady et al. |
| 5,048,515 A | 9/1991 | Sanso |
| 5,057,822 A | 10/1991 | Hoffman |
| 5,058,601 A | 10/1991 | Riker |
| 5,072,737 A | 12/1991 | Goulding |
| 5,074,297 A | 12/1991 | Venegas |
| 5,080,093 A | 1/1992 | Raabe et al. |
| 5,086,767 A | 2/1992 | Legal |
| 5,107,831 A | 4/1992 | Halpern et al. |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,137,026 A | 8/1992 | Waterson et al. |
| 5,148,802 A | 9/1992 | Sanders et al. |
| 5,150,291 A | 9/1992 | Cummings et al. |
| 5,156,145 A | 10/1992 | Flood et al. |
| 5,161,525 A | 11/1992 | Kimm et al. |
| 5,163,423 A | 11/1992 | Suzuki |
| 5,165,397 A | 11/1992 | Arp |
| 5,165,398 A | 11/1992 | Bird |
| 5,167,506 A | 12/1992 | Kilis et al. |
| 5,174,284 A | 12/1992 | Jackson |
| 5,195,512 A | 3/1993 | Rosso |
| 5,203,343 A | 4/1993 | Axe et al. |
| 5,211,170 A | 5/1993 | Press |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,239,995 A | 8/1993 | Estes et al. |
| 5,246,010 A | 9/1993 | Gazzara et al. |
| 5,251,632 A | 10/1993 | Delpy |
| 5,259,374 A | 11/1993 | Miller et al. |
| 5,261,397 A | 11/1993 | Grunstein |
| 5,261,415 A | 11/1993 | Dussault |
| 5,271,389 A | 12/1993 | Isaza et al. |
| 5,273,031 A | 12/1993 | Olsson et al. |
| 5,273,032 A | 12/1993 | Borody |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,303,700 A | 4/1994 | Weismann et al. |
| 5,307,794 A | 5/1994 | Rauterkus et al. |
| 5,307,795 A | 5/1994 | Whitwam et al. |
| 5,316,009 A | 5/1994 | Yamada |
| 5,318,017 A | 6/1994 | Ellison |
| 5,319,355 A | 6/1994 | Russek |
| 5,319,540 A | 6/1994 | Isaza et al. |
| 5,320,093 A | 6/1994 | Raemer |
| 5,322,057 A | 6/1994 | Raabe et al. |
| 5,322,059 A | 6/1994 | Walther |
| 5,323,772 A | 6/1994 | Linden et al. |
| 5,325,861 A | 7/1994 | Goulding |
| 5,333,106 A | 7/1994 | Lanpher et al. |
| 5,333,606 A | 8/1994 | Schneider et al. |
| 5,335,650 A | 8/1994 | Shaffer et al. |
| 5,339,807 A | 8/1994 | Carter |

(56) References Cited

U.S. PATENT DOCUMENTS

| | | |
|---|---|---|
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,842 A | 12/1994 | Olsson et al. |
| 5,373,851 A | 12/1994 | Reinhold, Jr. et al. |
| 5,383,448 A | 1/1995 | Tkatchouk et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,395,301 A | 3/1995 | Russek |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,471,977 A | 12/1995 | Olsson et al. |
| 5,474,062 A | 12/1995 | DeVires et al. |
| 5,477,860 A | 12/1995 | Essen Moller |
| 5,479,939 A | 1/1996 | Ogino |
| 5,485,833 A | 1/1996 | Dietz |
| 5,487,731 A | 1/1996 | Denton |
| 5,494,028 A | 2/1996 | DeVries et al. |
| 5,495,848 A | 3/1996 | Aylsworth et al. |
| 5,497,767 A | 3/1996 | Olsson et al. |
| 5,501,231 A | 3/1996 | Kaish |
| 5,503,146 A | 4/1996 | Froehlich et al. |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,522,382 A | 6/1996 | Sullivan et al. |
| 5,524,615 A | 6/1996 | Power |
| 5,524,616 A | 6/1996 | Smith et al. |
| 5,531,221 A | 7/1996 | Power |
| 5,534,851 A | 7/1996 | Russek |
| 5,537,992 A | 7/1996 | Bjoernstijerna et al. |
| 5,537,999 A | 7/1996 | Dearman et al. |
| 5,540,218 A | 7/1996 | Jones et al. |
| 5,540,220 A | 7/1996 | Gropper et al. |
| 5,542,410 A | 8/1996 | Goodman et al. |
| 5,542,415 A | 8/1996 | Brody |
| 5,542,416 A | 8/1996 | Chalvignac |
| 5,544,674 A | 8/1996 | Kelly |
| 5,549,106 A | 8/1996 | Gruenke et al. |
| 5,549,117 A | 8/1996 | Tacklind et al. |
| 5,551,418 A | 9/1996 | Estes et al. |
| 5,551,419 A | 9/1996 | Froehlich et al. |
| 5,553,620 A | 9/1996 | Snider et al. |
| 5,558,086 A | 9/1996 | Smith et al. |
| 5,560,353 A | 10/1996 | Willemot et al. |
| 5,562,918 A | 10/1996 | Stimpson |
| 5,564,414 A | 10/1996 | Walker et al. |
| 5,564,416 A | 10/1996 | Jones |
| 5,564,432 A | 10/1996 | Thomson |
| 5,571,142 A | 11/1996 | Brown et al. |
| 5,575,283 A | 11/1996 | Sjoestrand |
| 5,582,163 A | 12/1996 | Bonassa |
| 5,582,167 A | 12/1996 | Joseph |
| 5,582,182 A | 12/1996 | Hillsman |
| 5,590,648 A | 1/1997 | Mitchell et al. |
| 5,590,651 A | 1/1997 | Shaffer et al. |
| 5,591,130 A | 1/1997 | Denton |
| 5,596,983 A | 1/1997 | Zander et al. |
| 5,596,984 A | 1/1997 | O'Mahony et al. |
| 5,603,316 A | 2/1997 | Coufal et al. |
| 5,606,968 A | 3/1997 | Mang |
| 5,606,976 A | 3/1997 | Marshall et al. |
| 5,608,647 A | 3/1997 | Rubsamen et al. |
| 5,611,335 A | 3/1997 | Makhoul et al. |
| 5,626,144 A | 5/1997 | Tacklind et al. |
| 5,630,411 A | 5/1997 | Holscher |
| 5,632,269 A | 5/1997 | Zdrojkowski |
| 5,632,270 A | 5/1997 | O'Mahoney et al. |
| 5,632,281 A | 5/1997 | Rayburn |
| 5,634,461 A | 6/1997 | Faithfull et al. |
| 5,634,471 A | 6/1997 | Fairfax et al. |
| 5,642,726 A | 7/1997 | Owens et al. |
| 5,642,735 A | 7/1997 | Kolbly |
| 5,645,048 A | 7/1997 | Brodsky et al. |
| 5,647,346 A | 7/1997 | Holscher |
| 5,647,351 A | 7/1997 | Weismann et al. |
| 5,651,264 A | 7/1997 | Lo et al. |
| 5,651,361 A | 7/1997 | Dearman et al. |
| 5,655,516 A | 8/1997 | Goodman et al. |
| 5,655,519 A | 8/1997 | Alfery |
| 5,660,168 A | 8/1997 | Ottosson et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,685,318 A | 11/1997 | Elghazzawi |
| 5,687,713 A | 11/1997 | Bahr et al. |
| 5,692,497 A | 12/1997 | Schnitzer et al. |
| 5,694,924 A | 12/1997 | Cewers |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,715,812 A | 2/1998 | Deighan et al. |
| 5,720,276 A | 2/1998 | Kobatake et al. |
| 5,724,962 A | 3/1998 | Vidgren et al. |
| 5,724,990 A | 3/1998 | Ogino |
| 5,730,121 A | 3/1998 | Hawkins, Jr. et al. |
| 5,730,140 A | 3/1998 | Fitch |
| 5,730,145 A | 3/1998 | Defares et al. |
| 5,735,267 A | 4/1998 | Tobia |
| 5,735,287 A | 4/1998 | Thomson |
| 5,738,092 A | 4/1998 | Mock et al. |
| 5,740,792 A | 4/1998 | Ashley et al. |
| 5,740,797 A | 4/1998 | Dickson |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,765,558 A | 6/1998 | Psaros et al. |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |

(56) References Cited

U.S. PATENT DOCUMENTS

| | | |
|---|---|---|
| 5,794,986 A | 8/1998 | Gansel et al. |
| 5,800,361 A | 9/1998 | Rayburn |
| 5,803,065 A | 9/1998 | Zdrojkowski et al. |
| 5,806,512 A | 9/1998 | Abramov et al. |
| 5,806,514 A | 9/1998 | Mock et al. |
| 5,807,245 A | 9/1998 | Aldestam et al. |
| 5,809,997 A | 9/1998 | Wolf |
| 5,810,000 A | 9/1998 | Stevens |
| 5,810,741 A | 9/1998 | Essen Moller |
| 5,813,397 A | 9/1998 | Goodman et al. |
| 5,813,399 A | 9/1998 | Isaza et al. |
| 5,813,401 A | 9/1998 | Radcliff et al. |
| 5,814,086 A | 9/1998 | Hirschberg et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,832,916 A | 11/1998 | Lundberg |
| 5,832,919 A | 11/1998 | Kano et al. |
| 5,839,430 A | 11/1998 | Cama |
| 5,860,418 A | 1/1999 | Lundberg |
| 5,864,938 A | 2/1999 | Gansel et al. |
| 5,865,168 A | 2/1999 | Isaza |
| 5,865,171 A | 2/1999 | Cinquin |
| 5,865,174 A | 2/1999 | Kloeppel |
| 5,868,133 A | 2/1999 | DeVries et al. |
| 5,875,777 A | 3/1999 | Eriksson |
| 5,876,352 A | 3/1999 | Weismann |
| 5,876,353 A | 3/1999 | Riff |
| 5,878,744 A | 3/1999 | Pfeiffer |
| 5,881,717 A | 3/1999 | Isaza |
| 5,881,723 A | 3/1999 | Wallace et al. |
| 5,881,725 A | 3/1999 | Hoffman et al. |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,906,203 A | 5/1999 | Klockseth et al. |
| 5,909,731 A | 6/1999 | O'Mahony et al. |
| 5,911,218 A | 6/1999 | DiMarco |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,931,160 A | 8/1999 | Gilmore et al. |
| 5,931,162 A | 8/1999 | Christian |
| 5,932,812 A | 8/1999 | Delsing |
| 5,934,274 A | 8/1999 | Merrick et al. |
| 5,937,853 A | 8/1999 | Strom |
| 5,937,854 A | 8/1999 | Stenzler |
| 5,944,680 A | 8/1999 | Christopherson |
| 5,956,501 A | 9/1999 | Brown |
| 5,957,861 A | 9/1999 | Combs et al. |
| 5,964,218 A | 10/1999 | Smith et al. |
| 5,970,975 A | 10/1999 | Estes et al. |
| 5,971,937 A | 10/1999 | Ekstrom |
| 5,975,081 A | 11/1999 | Hood et al. |
| 5,979,440 A | 11/1999 | Honkonen et al. |
| 5,980,466 A | 11/1999 | Thomson |
| 5,996,580 A | 12/1999 | Swann |
| 6,000,396 A | 12/1999 | Melker et al. |
| 6,012,450 A | 1/2000 | Rubsamen |
| 6,015,388 A | 1/2000 | Sackner et al. |
| 6,017,315 A | 1/2000 | Starr et al. |
| 6,019,100 A | 2/2000 | Alving et al. |
| 6,024,089 A | 2/2000 | Wallace et al. |
| 6,026,323 A | 2/2000 | Skladnev et al. |
| 6,029,660 A | 2/2000 | Calluaud et al. |
| 6,029,664 A | 2/2000 | Zdrojkowski et al. |
| 6,032,119 A | 2/2000 | Brown et al. |
| 6,041,780 A | 3/2000 | Richard et al. |
| 6,047,860 A | 4/2000 | Sanders |
| 6,055,506 A | 4/2000 | Frasca, Jr. |
| 6,055,981 A | 5/2000 | Laswick et al. |
| 6,068,602 A | 5/2000 | Tham et al. |
| 6,073,110 A | 6/2000 | Rhodes et al. |
| 6,076,523 A | 6/2000 | Jones et al. |
| 6,095,140 A | 8/2000 | Poon et al. |
| 6,099,481 A | 8/2000 | Daniels et al. |
| 6,106,481 A | 8/2000 | Cohen |
| 6,109,259 A | 8/2000 | Fitzgerald |
| 6,109,260 A | 8/2000 | Bathe |
| 6,112,744 A | 9/2000 | Hognelid |
| 6,116,240 A | 9/2000 | Merrick et al. |
| 6,116,464 A | 9/2000 | Sanders |
| 6,118,847 A | 9/2000 | Hernandez-Guerra et al. |
| 6,119,684 A | 9/2000 | Nohl et al. |
| 6,123,073 A | 9/2000 | Schlawin et al. |
| 6,131,571 A | 10/2000 | Lampotang et al. |
| 6,131,572 A | 10/2000 | Heinonen |
| 6,135,105 A | 10/2000 | Lampotang et al. |
| 6,135,106 A | 10/2000 | Dirks et al. |
| 6,139,506 A | 10/2000 | Heinonen |
| 6,142,150 A | 11/2000 | O'Mahony et al. |
| 6,148,814 A | 11/2000 | Clemmer et al. |
| 6,148,815 A | 11/2000 | Wolf |
| 6,152,129 A | 11/2000 | Jones |
| 6,152,133 A | 11/2000 | Psaros et al. |
| 6,152,135 A | 11/2000 | DeVries et al. |
| 6,155,257 A | 12/2000 | Lurie et al. |
| 6,158,432 A | 12/2000 | Biondi et al. |
| 6,158,433 A | 12/2000 | Ong et al. |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,192,885 B1 | 2/2001 | Jalde |
| 6,196,222 B1 | 3/2001 | Heinonen et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,119 B1 | 4/2001 | Brydon et al. |
| 6,213,120 B1 | 4/2001 | Block et al. |
| 6,213,955 B1 | 4/2001 | Karakasoglu et al. |
| 6,216,690 B1 | 4/2001 | Keitel et al. |
| 6,220,245 B1 | 4/2001 | Takabayashi et al. |
| 6,223,744 B1 | 5/2001 | Garon |
| 6,224,553 B1 | 5/2001 | Nevo |
| 6,227,197 B1 | 5/2001 | Fitzgerald |
| 6,230,708 B1 | 5/2001 | Radko |
| 6,233,539 B1 | 5/2001 | Brown |
| 6,234,963 B1 | 5/2001 | Blike et al. |
| 6,240,920 B1 | 6/2001 | Ström |
| 6,251,082 B1 | 6/2001 | Rayburn |
| 6,257,234 B1 | 7/2001 | Sun |
| 6,258,039 B1 | 7/2001 | Okamoto et al. |
| 6,260,549 B1 | 7/2001 | Sosiak |
| 6,261,238 B1 | 7/2001 | Gavriely |
| 6,269,810 B1 | 8/2001 | Brooker et al. |
| 6,269,812 B1 | 8/2001 | Wallace et al. |
| 6,273,088 B1 | 8/2001 | Hillsman |
| 6,273,444 B1 | 8/2001 | Power |
| 6,279,569 B1 | 8/2001 | Berthon Jones |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 | 10/2001 | Wallace et al. |
| 6,305,374 B1 | 10/2001 | Zdrojkowski et al. |
| 6,308,703 B1 | 10/2001 | Alving et al. |

(56) References Cited

U.S. PATENT DOCUMENTS

| | | |
|---|---|---|
| 6,308,706 B1 | 10/2001 | Lammers et al. |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,339,410 B1 | 1/2002 | Milner et al. |
| 6,340,348 B1 | 1/2002 | Krishnan et al. |
| 6,341,604 B1 | 1/2002 | Kellon |
| 6,342,040 B1 | 1/2002 | Starr et al. |
| 6,343,603 B1 | 2/2002 | Tuck et al. |
| 6,345,619 B1 | 2/2002 | Finn |
| 6,349,722 B1 | 2/2002 | Gradon et al. |
| 6,349,724 B1 | 2/2002 | Burton et al. |
| 6,355,002 B1 | 3/2002 | Faram et al. |
| 6,357,438 B1 | 3/2002 | Hansen |
| 6,360,740 B1 | 3/2002 | Ward et al. |
| 6,360,745 B1 | 3/2002 | Wallace et al. |
| 6,362,620 B1 | 3/2002 | Debbins et al. |
| 6,367,475 B1 | 4/2002 | Kofoed et al. |
| 6,369,838 B1 | 4/2002 | Wallace et al. |
| 6,370,419 B2 | 4/2002 | Lampotang et al. |
| 6,377,046 B1 | 4/2002 | Debbins et al. |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,390,988 B1 | 5/2002 | Robinson |
| 6,397,838 B1 | 6/2002 | Zimlich, Jr. et al. |
| 6,402,698 B1 | 6/2002 | Mault |
| 6,408,043 B1 | 6/2002 | Hu et al. |
| 6,408,847 B1 | 6/2002 | Nuckols et al. |
| 6,412,482 B1 | 7/2002 | Rowe |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,425,392 B1 | 7/2002 | Sosiak |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,446,630 B1 | 9/2002 | Todd, Jr. |
| 6,450,164 B1 | 9/2002 | Banner et al. |
| 6,450,968 B1 | 9/2002 | Wallen et al. |
| 6,454,708 B1 | 9/2002 | Ferguson et al. |
| 6,457,472 B1 | 10/2002 | Schwartz et al. |
| 6,459,933 B1 | 10/2002 | Lurie et al. |
| 6,461,315 B1 | 10/2002 | Gattinoni |
| 6,463,930 B2 | 10/2002 | Biondi et al. |
| 6,467,477 B1 | 10/2002 | Frank et al. |
| 6,467,478 B1 | 10/2002 | Merrick et al. |
| 6,467,479 B1 | 10/2002 | Albert et al. |
| 6,467,481 B1 | 10/2002 | Eswarappa |
| 6,471,658 B1 | 10/2002 | Daniels et al. |
| 6,484,719 B1 | 11/2002 | Berthon Jones |
| 6,488,029 B1 | 12/2002 | Hood et al. |
| 6,488,629 B1 | 12/2002 | Saetre et al. |
| 6,494,201 B1 | 12/2002 | Welik |
| RE37,970 E | 1/2003 | Costello, Jr. |
| 6,511,426 B1 | 1/2003 | Hossack et al. |
| 6,512,938 B2 | 1/2003 | Claure et al. |
| 6,515,683 B1 | 2/2003 | Wright |
| 6,516,800 B1 | 2/2003 | Bowden |
| 6,517,497 B2 | 2/2003 | Rymut et al. |
| 6,523,538 B1 | 2/2003 | Wikfeldt |
| 6,526,970 B2 | 3/2003 | DeVries et al. |
| 6,532,956 B2 | 3/2003 | Hill |
| 6,532,957 B2 | 3/2003 | Berthon Jones |
| 6,532,959 B1 | 3/2003 | Berthon Jones |
| 6,533,723 B1 | 3/2003 | Lockery et al. |
| 6,533,730 B2 | 3/2003 | Strom |
| 6,536,433 B1 | 3/2003 | Cewers |
| 6,539,938 B2 | 4/2003 | Weinstein et al. |
| 6,539,940 B2 | 4/2003 | Zdrojkowski et al. |
| 6,543,449 B1 | 4/2003 | Woodring et al. |
| 6,543,701 B1 | 4/2003 | Ho |
| 6,544,192 B2 | 4/2003 | Starr et al. |
| 6,546,930 B1 | 4/2003 | Emerson et al. |
| 6,547,728 B1 | 4/2003 | Cornuejols |
| 6,547,743 B2 | 4/2003 | Brydon |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,564,798 B1 | 5/2003 | Jalde |
| 6,566,875 B1 | 5/2003 | Hasson et al. |
| 6,571,122 B2 | 5/2003 | Schroeppel et al. |
| 6,571,795 B2 | 6/2003 | Bourdon |
| 6,571,796 B2 | 6/2003 | Banner et al. |
| 6,575,163 B1 | 6/2003 | Berthon Jones |
| 6,575,164 B1 | 6/2003 | Jaffe et al. |
| 6,577,884 B1 | 6/2003 | Boas |
| 6,578,575 B1 | 6/2003 | Jonson |
| 6,581,592 B1 | 6/2003 | Bathe et al. |
| 6,581,599 B1 | 6/2003 | Stenzler |
| 6,584,973 B1 | 7/2003 | Biondi et al. |
| 6,588,423 B1 | 7/2003 | Sinderby |
| 6,595,213 B2 | 7/2003 | Bennarsten |
| 6,597,939 B1 | 7/2003 | Lampotang et al. |
| 6,599,252 B2 | 7/2003 | Starr |
| 6,601,583 B2 | 8/2003 | Pessala et al. |
| 6,603,494 B1 | 8/2003 | Banks et al. |
| 6,606,993 B1 | 8/2003 | Wiesmann et al. |
| 6,607,481 B1 | 8/2003 | Clawson |
| 6,609,517 B1 | 8/2003 | Estes et al. |
| 6,609,518 B2 | 8/2003 | Lamb |
| 6,620,106 B2 | 9/2003 | Mault |
| 6,621,917 B1 | 9/2003 | Vilser |
| 6,622,726 B1 | 9/2003 | Du |
| 6,626,175 B2 | 9/2003 | Jafari et al. |
| 6,629,934 B2 | 10/2003 | Mault et al. |
| 6,630,176 B2 | 10/2003 | Li et al. |
| 6,631,716 B1 | 10/2003 | Robinson et al. |
| 6,631,717 B1 | 10/2003 | Rich et al. |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger et al. |
| 6,651,652 B1 | 11/2003 | Ward |
| 6,651,653 B1 | 11/2003 | Honkonen et al. |
| 6,651,657 B1 | 11/2003 | Manigel et al. |
| 6,655,383 B1 | 12/2003 | Lundberg |
| 6,656,129 B2 | 12/2003 | Niles et al. |
| 6,659,101 B2 | 12/2003 | Jones |
| 6,659,961 B2 | 12/2003 | Robinson |
| 6,668,824 B1 | 12/2003 | Isaza et al. |
| 6,668,829 B2 | 12/2003 | Biondi et al. |
| 6,671,529 B2 | 12/2003 | Claure et al. |
| 6,673,018 B2 | 1/2004 | Friedman |
| 6,675,801 B2 | 1/2004 | Wallace et al. |
| 6,679,258 B1 | 1/2004 | Strom |
| 6,681,643 B2 | 1/2004 | Heinonen |
| 6,681,764 B1 | 1/2004 | Honkonen et al. |
| 6,688,307 B2 | 2/2004 | Berthon Jones |
| 6,689,091 B2 | 2/2004 | Bui et al. |
| 6,694,978 B1 | 2/2004 | Bennarsten |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B2 | 4/2004 | Blomberg |
| 6,722,360 B2 | 4/2004 | Doshi |
| 6,725,077 B1 | 4/2004 | Balloni et al. |
| 6,725,447 B1 | 4/2004 | Gilman et al. |
| 6,725,860 B2 | 4/2004 | Wallroth et al. |
| 6,726,598 B1 | 4/2004 | Jarvis et al. |
| 6,733,449 B1 | 5/2004 | Krishnamurthy et al. |
| 6,738,079 B1 | 5/2004 | Kellerman et al. |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |

(56) References Cited

U.S. PATENT DOCUMENTS

| | | |
|---|---|---|
| 6,745,764 B2 | 6/2004 | Hickle |
| 6,745,771 B2 | 6/2004 | Castor et al. |
| 6,745,773 B1 | 6/2004 | Gobel |
| 6,752,766 B2 | 6/2004 | Kowallik et al. |
| 6,752,772 B2 | 6/2004 | Kahn |
| 6,755,193 B2 | 6/2004 | Berthon-Jones et al. |
| 6,755,787 B2 | 6/2004 | Hossack et al. |
| 6,758,216 B1 | 7/2004 | Berthon Jones et al. |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,776,159 B2 | 8/2004 | Pelerossi et al. |
| 6,782,888 B1 | 8/2004 | Friberg et al. |
| 6,786,217 B2 | 9/2004 | Stenzler |
| 6,790,178 B1 | 9/2004 | Mault et al. |
| 6,792,066 B1 | 9/2004 | Harder et al. |
| 6,796,305 B1 | 9/2004 | Banner et al. |
| 6,801,227 B2 | 10/2004 | Bocionek et al. |
| 6,801,802 B2 | 10/2004 | Sitzman et al. |
| 6,805,118 B2 | 10/2004 | Brooker et al. |
| 6,807,965 B1 | 10/2004 | Hickle |
| 6,810,876 B2 | 11/2004 | Jones |
| 6,814,074 B1 | 11/2004 | Nadjafizadeh et al. |
| 6,814,075 B2 | 11/2004 | Boussignac |
| 6,820,613 B2 | 11/2004 | Wenkebach et al. |
| 6,820,614 B2 | 11/2004 | Bonutti |
| 6,820,618 B2 | 11/2004 | Banner et al. |
| 6,822,223 B2 | 11/2004 | Davis |
| 6,823,866 B2 | 11/2004 | Jafari et al. |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,241 B2 | 1/2005 | Samzelius |
| 6,837,242 B2 | 1/2005 | Younes |
| 6,839,753 B2 | 1/2005 | Biondi et al. |
| 6,840,240 B1 | 1/2005 | Berthon-Jones et al. |
| 6,845,773 B2 | 1/2005 | Berthon-Jones et al. |
| 6,848,444 B2 | 2/2005 | Smith et al. |
| 6,851,427 B1 | 2/2005 | Nashed |
| 6,858,006 B2 | 2/2005 | MacCarter et al. |
| 6,860,264 B2 | 3/2005 | Christopher |
| 6,860,265 B1 | 3/2005 | Emerson |
| 6,860,266 B2 | 3/2005 | Blike |
| 6,860,858 B2 | 3/2005 | Green et al. |
| 6,866,040 B1 | 3/2005 | Bourdon |
| 6,866,629 B2 | 3/2005 | Bardy |
| 6,877,511 B2 | 4/2005 | DeVries et al. |
| 6,893,397 B2 | 5/2005 | Bardy |
| 6,899,101 B2 | 5/2005 | Haston et al. |
| 6,899,103 B1 | 5/2005 | Hood et al. |
| 6,899,683 B2 | 5/2005 | Mault et al. |
| 6,899,684 B2 | 5/2005 | Mault et al. |
| 6,910,480 B1 | 6/2005 | Berthon Jones |
| 6,910,481 B2 | 6/2005 | Kimmel et al. |
| 6,920,875 B1 | 7/2005 | Hill et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry et al. |
| 6,947,780 B2 | 9/2005 | Scharf |
| 6,948,497 B2 | 9/2005 | Zdrojkowski et al. |
| 6,949,133 B2 | 9/2005 | McCombs et al. |
| 6,951,217 B2 | 10/2005 | Jones |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi et al. |
| 6,976,487 B1 | 12/2005 | Melker et al. |
| 6,976,958 B2 | 12/2005 | Quy |
| 6,986,347 B2 | 1/2006 | Hickle |
| 6,990,977 B1 | 1/2006 | Calluaud et al. |
| 6,990,980 B2 | 1/2006 | Richey, II |
| 6,997,185 B2 | 2/2006 | Han et al. |
| 6,997,880 B2 | 2/2006 | Carlebach et al. |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,008,380 B1 | 3/2006 | Rees et al. |
| 7,011,091 B2 | 3/2006 | Hill et al. |
| 7,013,892 B2 | 3/2006 | Estes et al. |
| 7,017,574 B2 | 3/2006 | Biondi et al. |
| 7,019,652 B2 | 3/2006 | Richardson |
| 7,033,323 B2 | 4/2006 | Botbol et al. |
| 7,036,504 B2 | 5/2006 | Wallace et al. |
| 7,039,878 B2 | 5/2006 | Auer et al. |
| 7,040,315 B1 | 5/2006 | Strömberg |
| 7,040,318 B2 | 5/2006 | Däscher et al. |
| 7,040,320 B2 | 5/2006 | Fjeld et al. |
| 7,040,321 B2 | 5/2006 | Gobel et al. |
| 7,046,254 B2 | 5/2006 | Brown et al. |
| 7,047,092 B2 | 5/2006 | Wimsatt |
| 7,051,736 B2 | 5/2006 | Banner et al. |
| 7,055,522 B2 | 6/2006 | Berthon Jones |
| 7,062,251 B2 | 6/2006 | Birkett et al. |
| 7,066,173 B2 | 6/2006 | Banner et al. |
| 7,066,176 B2 | 6/2006 | Jaffe et al. |
| 7,077,125 B2 | 7/2006 | Scheuch |
| 7,077,131 B2 | 7/2006 | Hansen |
| 7,077,132 B2 | 7/2006 | Berthon Jones |
| 7,080,646 B2 | 7/2006 | Wiesmann et al. |
| 7,081,091 B2 | 7/2006 | Merrett et al. |
| 7,081,095 B2 | 7/2006 | Lynn et al. |
| RE39,225 E | 8/2006 | Isaza et al. |
| 7,083,574 B2 | 8/2006 | Kline |
| 7,089,927 B2 | 8/2006 | John et al. |
| 7,089,930 B2 | 8/2006 | Adams et al. |
| 7,089,937 B2 | 8/2006 | Berthon Jones et al. |
| 7,094,208 B2 | 8/2006 | Williams et al. |
| 7,100,607 B2 | 9/2006 | Zdrojkowski et al. |
| 7,100,609 B2 | 9/2006 | Berthon Jones et al. |
| 7,116,810 B2 | 10/2006 | Miller et al. |
| 7,117,438 B2 | 10/2006 | Wallace et al. |
| 7,121,277 B2 | 10/2006 | Ström |
| 7,128,069 B2 | 10/2006 | Farrugia et al. |
| 7,128,578 B2 | 10/2006 | Lampotang et al. |
| 7,137,389 B2 | 11/2006 | Berthon Jones |
| 7,147,600 B2 | 12/2006 | Bardy |
| 7,156,095 B2 | 1/2007 | Melker et al. |
| 7,156,808 B2 | 1/2007 | Quy |
| 7,162,296 B2 | 1/2007 | Leonhardt et al. |
| 7,164,972 B2 | 1/2007 | Imhof et al. |
| 7,165,221 B2 | 1/2007 | Monteleone et al. |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol et al. |
| 7,188,621 B2 | 3/2007 | DeVries et al. |
| 7,191,780 B2 | 3/2007 | Faram |
| 7,201,734 B2 | 4/2007 | Hickle |
| 7,203,353 B2 | 4/2007 | Klotz et al. |
| 7,210,478 B2 | 5/2007 | Banner et al. |
| 7,211,049 B2 | 5/2007 | Bradley et al. |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,226,427 B2 | 6/2007 | Steen |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,255,103 B2 | 8/2007 | Bassin |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |

(56) References Cited

U.S. PATENT DOCUMENTS

| | | |
|---|---|---|
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,334,581 B2 | 2/2008 | Doshi |
| 7,343,916 B2 | 3/2008 | Biondo et al. |
| 7,343,917 B2 | 3/2008 | Jones |
| 7,347,200 B2 | 3/2008 | Jones et al. |
| 7,347,204 B1 | 3/2008 | Lindsey et al. |
| 7,347,205 B2 | 3/2008 | Levi |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,363,925 B2 | 4/2008 | Pagan |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,015 B2 | 9/2008 | Delisle et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,445,006 B2 | 11/2008 | Dhuper et al. |
| 7,448,383 B2 | 11/2008 | Delache et al. |
| 7,452,333 B2 | 11/2008 | Roteliuk |
| 7,455,583 B2 | 11/2008 | Taya |
| 7,460,959 B2 | 12/2008 | Jafari |
| 7,464,339 B2 | 12/2008 | Keenan, Jr. et al. |
| 7,464,711 B2 | 12/2008 | Flodin |
| 7,469,698 B1 | 12/2008 | Childers et al. |
| 7,484,508 B2 | 2/2009 | Younes |
| 7,487,773 B2 | 2/2009 | Li |
| 7,487,774 B2 | 2/2009 | Acker |
| 7,487,775 B2 | 2/2009 | Mashak |
| 7,490,085 B2 | 2/2009 | Walker et al. |
| 7,495,546 B2 | 2/2009 | Lintell et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,509,957 B2 | 3/2009 | Duquette et al. |
| 7,512,450 B2 | 3/2009 | Ahmed |
| 7,512,593 B2 | 3/2009 | Karklins et al. |
| 7,523,752 B2 | 4/2009 | Montgomery et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,549,421 B2 | 6/2009 | Levi et al. |
| 7,552,731 B2 | 6/2009 | Jorczak et al. |
| 7,556,036 B2 | 7/2009 | Bouillon et al. |
| 7,556,038 B2 | 7/2009 | Kirby et al. |
| 7,559,326 B2 | 7/2009 | Smith et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,572,225 B2 | 8/2009 | Stahmann et al. |
| 7,574,246 B2 | 8/2009 | Krebs et al. |
| 7,584,712 B2 | 9/2009 | Lu |
| 7,584,752 B2 | 9/2009 | Garber et al. |
| 7,588,033 B2 | 9/2009 | Wondka |
| 7,588,543 B2 | 9/2009 | Euliano et al. |
| 7,590,551 B2 | 9/2009 | Auer |
| 7,591,830 B2 | 9/2009 | Rutter |
| 7,594,508 B2 | 9/2009 | Doyle |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,914 B2 | 11/2009 | Bolam et al. |
| 7,610,915 B2 | 11/2009 | Dittmann |
| 7,617,821 B2 | 11/2009 | Hughes |
| 7,617,824 B2 | 11/2009 | Doyle |
| 7,617,825 B2 | 11/2009 | Pedemonte |
| 7,618,378 B2 | 11/2009 | Bingham et al. |
| 7,624,736 B2 | 12/2009 | Borody |
| 7,625,345 B2 | 12/2009 | Quinn |
| 7,628,151 B2 | 12/2009 | Bassin |
| 7,630,755 B2 | 12/2009 | Stahmann et al. |
| 7,634,998 B1 | 12/2009 | Fenley |
| 7,644,713 B2 | 1/2010 | Berthon Jones |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,594 B2 | 3/2010 | Downie |
| 7,669,598 B2 | 3/2010 | Rick et al. |
| 7,671,733 B2 | 3/2010 | McNeal et al. |
| 7,678,061 B2 | 3/2010 | Lee et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,694,682 B2 | 4/2010 | Petersen et al. |
| 7,698,156 B2 | 4/2010 | Martucci et al. |
| 7,708,015 B2 | 5/2010 | Seeger et al. |
| 7,717,110 B2 | 5/2010 | Kane et al. |
| 7,717,112 B2 | 5/2010 | Sun et al. |
| 7,717,113 B2 | 5/2010 | Andrieux |
| 7,721,736 B2 | 5/2010 | Urias et al. |
| 7,722,546 B2 | 5/2010 | Madaus et al. |
| D618,356 S | 6/2010 | Ross |
| 7,727,160 B2 | 6/2010 | Green et al. |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,775,207 B2 | 8/2010 | Jaffe et al. |
| 7,778,709 B2 | 8/2010 | Gollasch et al. |
| 7,778,851 B2 | 8/2010 | Schoenberg et al. |
| 7,779,834 B2 | 8/2010 | Calluaud et al. |
| 7,784,461 B2 | 8/2010 | Figueiredo et al. |
| 7,785,263 B2 | 8/2010 | Roteliuk et al. |
| 7,785,265 B2 | 8/2010 | Schatzl |
| 7,793,659 B2 | 9/2010 | Breen |
| 7,793,660 B2 | 9/2010 | Kimmel et al. |
| 7,798,145 B2 | 9/2010 | Weismann et al. |
| 7,802,571 B2 | 9/2010 | Tehrani |
| 7,809,442 B2 | 10/2010 | Bolea et al. |

(56) References Cited

U.S. PATENT DOCUMENTS

| | | |
|---|---|---|
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,841,341 B2 | 11/2010 | Dhuper et al. |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,865,244 B2 | 1/2011 | Giftakis et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,905,231 B2 | 3/2011 | Chalvignac |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,711 B2 | 8/2011 | Wood et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 10,362,967 B2 | 7/2019 | Milne |
| 2001/0004893 A1 | 6/2001 | Biondi et al. |
| 2001/0007255 A1 | 7/2001 | Stumpf |
| 2001/0035186 A1 | 11/2001 | Hill |
| 2001/0056358 A1 | 12/2001 | Dulong et al. |
| 2002/0023640 A1 | 2/2002 | Nightengale |
| 2002/0026941 A1 | 3/2002 | Biondi et al. |
| 2002/0044059 A1 | 4/2002 | Reeder et al. |
| 2002/0046753 A1 | 4/2002 | Lamb |
| 2002/0053345 A1 | 5/2002 | Jafari et al. |
| 2002/0073993 A1 | 6/2002 | Weinstein et al. |
| 2002/0077863 A1 | 6/2002 | Rutledge et al. |
| 2002/0091548 A1 | 7/2002 | Auer et al. |
| 2002/0153006 A1 | 10/2002 | Zimlich et al. |
| 2002/0153009 A1 | 10/2002 | Chornyj et al. |
| 2002/0174866 A1 | 11/2002 | Orr et al. |
| 2002/0177758 A1 | 11/2002 | Schoenberg et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0050568 A1 | 3/2003 | Green et al. |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0125662 A1 | 7/2003 | Bui |
| 2003/0130567 A1 | 7/2003 | Mault et al. |
| 2003/0130595 A1 | 7/2003 | Mault |
| 2003/0131848 A1 | 7/2003 | Stenzler |
| 2003/0136402 A1 | 7/2003 | Jiang et al. |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0176804 A1 | 9/2003 | Melker |
| 2003/0178024 A1 | 9/2003 | Allan et al. |
| 2003/0192542 A1 | 10/2003 | Isaza |
| 2003/0192544 A1 | 10/2003 | Jones et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avraham et al. |
| 2003/0208465 A1 | 11/2003 | Yurko et al. |
| 2003/0222548 A1 | 12/2003 | Richardson et al. |
| 2003/0230308 A1 | 12/2003 | Linden |
| 2004/0003814 A1 | 1/2004 | Banner et al. |
| 2004/0010425 A1 | 1/2004 | Wilkes et al. |
| 2004/0016431 A1 | 1/2004 | Preveyraud |
| 2004/0034289 A1 | 2/2004 | Teller et al. |
| 2004/0040560 A1 | 3/2004 | Euliano et al. |
| 2004/0050387 A1 | 3/2004 | Younes |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0103896 A1 | 6/2004 | Jafari et al. |
| 2004/0121767 A1 | 6/2004 | Simpson et al. |
| 2004/0122294 A1 | 6/2004 | Hatlestad et al. |
| 2004/0149282 A1 | 8/2004 | Hickle |
| 2004/0150525 A1 | 8/2004 | Wilson et al. |
| 2004/0159323 A1 | 8/2004 | Schmidt et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0224293 A1 | 11/2004 | Penning et al. |
| 2004/0231670 A1 | 11/2004 | Bassin |
| 2004/0236240 A1 | 11/2004 | Kraus et al. |
| 2004/0249673 A1 | 12/2004 | Smith |
| 2005/0016534 A1 | 1/2005 | Ost |
| 2005/0022809 A1 | 2/2005 | Wondka |
| 2005/0027252 A1 | 2/2005 | Boukas |
| 2005/0033198 A1 | 2/2005 | Kehyayan et al. |

(56) References Cited

U.S. PATENT DOCUMENTS

| | | |
|---|---|---|
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0061318 A1 | 3/2005 | Faram |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0076907 A1 | 4/2005 | Stenzler |
| 2005/0085869 A1 | 4/2005 | Tehran et al. |
| 2005/0098179 A1 | 5/2005 | Burton et al. |
| 2005/0103331 A1 | 5/2005 | Wedemeyer |
| 2005/0108057 A1 | 5/2005 | Cohen et al. |
| 2005/0109339 A1 | 5/2005 | Stahmann et al. |
| 2005/0109340 A1 | 5/2005 | Tehrani |
| 2005/0112013 A1 | 5/2005 | DeVries et al. |
| 2005/0112325 A1 | 5/2005 | Hickle |
| 2005/0121035 A1 | 6/2005 | Martin |
| 2005/0124866 A1 | 6/2005 | Elaz et al. |
| 2005/0126565 A1 | 6/2005 | Huang |
| 2005/0133027 A1 | 6/2005 | Elaz et al. |
| 2005/0133028 A1 | 6/2005 | Pagan |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0199237 A1 | 9/2005 | Lurie |
| 2005/0204310 A1 | 9/2005 | De Zwart et al. |
| 2005/0215904 A1 | 9/2005 | Sumanaweera et al. |
| 2005/0217671 A1 | 10/2005 | Fisher et al. |
| 2005/0217674 A1 | 10/2005 | Burton et al. |
| 2005/0241639 A1 | 11/2005 | Zilberg |
| 2005/0251040 A1 | 11/2005 | Relkuntwar et al. |
| 2005/0263152 A1 | 12/2005 | Fong |
| 2005/0279358 A1 | 12/2005 | Richey, II |
| 2005/0284469 A1 | 12/2005 | Tobia et al. |
| 2005/0288571 A1 | 12/2005 | Perkins et al. |
| 2006/0009708 A1 | 1/2006 | Rapoport et al. |
| 2006/0011195 A1 | 1/2006 | Zarychta |
| 2006/0032497 A1 | 2/2006 | Doshi |
| 2006/0037614 A1 | 2/2006 | Madaus et al. |
| 2006/0047202 A1 | 3/2006 | Elliott |
| 2006/0060198 A1 | 3/2006 | Aylsworth et al. |
| 2006/0078867 A1 | 4/2006 | Penny et al. |
| 2006/0079799 A1 | 4/2006 | Green et al. |
| 2006/0080140 A1 | 4/2006 | Buttner et al. |
| 2006/0080343 A1 | 4/2006 | Carter et al. |
| 2006/0094972 A1 | 5/2006 | Drew |
| 2006/0102171 A1 | 5/2006 | Gavish |
| 2006/0102180 A1 | 5/2006 | Jones |
| 2006/0122474 A1 | 6/2006 | Teller et al. |
| 2006/0129055 A1 | 6/2006 | Orr et al. |
| 2006/0142815 A1 | 6/2006 | Tehran et al. |
| 2006/0144396 A1 | 7/2006 | DeVries et al. |
| 2006/0144397 A1 | 7/2006 | Wallace et al. |
| 2006/0149144 A1 | 7/2006 | Lynn et al. |
| 2006/0149589 A1 | 7/2006 | Wager |
| 2006/0150974 A1 | 7/2006 | Berthon-Jones |
| 2006/0150982 A1 | 7/2006 | Wood |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0162727 A1 | 7/2006 | Biondi et al. |
| 2006/0173257 A1 | 8/2006 | Nagai et al. |
| 2006/0174884 A1 | 8/2006 | Habashi |
| 2006/0178245 A1 | 8/2006 | Schiller et al. |
| 2006/0178591 A1 | 8/2006 | Hempfling |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0200009 A1 | 9/2006 | Wekell et al. |
| 2006/0201507 A1 | 9/2006 | Breen |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0243275 A1 | 11/2006 | Ruckdeschel et al. |
| 2006/0249148 A1 | 11/2006 | Younes |
| 2006/0249151 A1 | 11/2006 | Gambone |
| 2006/0249153 A1 | 11/2006 | DeVries et al. |
| 2006/0249155 A1 | 11/2006 | Gambone |
| 2006/0264762 A1 | 11/2006 | Starr |
| 2006/0272642 A1 | 12/2006 | Chalvignac |
| 2006/0272643 A1 | 12/2006 | Aylsworth et al. |
| 2006/0276718 A1 | 12/2006 | Madaus et al. |
| 2006/0278221 A1 | 12/2006 | Schermeier et al. |
| 2006/0278222 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017510 A1 | 1/2007 | Riedo |
| 2007/0017515 A1 | 1/2007 | Wallace et al. |
| 2007/0017518 A1 | 1/2007 | Farrugia et al. |
| 2007/0021673 A1 | 1/2007 | Arbel et al. |
| 2007/0028920 A1 | 2/2007 | Acker |
| 2007/0028921 A1 | 2/2007 | Banner et al. |
| 2007/0038081 A1 | 2/2007 | Eck et al. |
| 2007/0044796 A1 | 3/2007 | Zdrojkowski et al. |
| 2007/0044805 A1 | 3/2007 | Wedler et al. |
| 2007/0060812 A1 | 3/2007 | Harel et al. |
| 2007/0062529 A1 | 3/2007 | Choncholas et al. |
| 2007/0062530 A1 | 3/2007 | Weismann et al. |
| 2007/0062532 A1 | 3/2007 | Choncholas |
| 2007/0062533 A1 | 3/2007 | Choncholas et al. |
| 2007/0066961 A1 | 3/2007 | Rutter |
| 2007/0073169 A1 | 3/2007 | Averina et al. |
| 2007/0073181 A1 | 3/2007 | Pu et al. |
| 2007/0077200 A1 | 4/2007 | Baker |
| 2007/0089738 A1 | 4/2007 | Soliman et al. |
| 2007/0113843 A1 | 5/2007 | Hughes |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0144521 A1 | 6/2007 | DeVries et al. |
| 2007/0144523 A1 | 6/2007 | Bolam et al. |
| 2007/0149860 A1 | 6/2007 | Lynn et al. |
| 2007/0151563 A1 | 7/2007 | Ozaki et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0163590 A1 | 7/2007 | Bassin |
| 2007/0167853 A1 | 7/2007 | Melker et al. |
| 2007/0179357 A1 | 8/2007 | Bardy |
| 2007/0181122 A1 | 8/2007 | Mulier |
| 2007/0185390 A1 | 8/2007 | Perkins et al. |
| 2007/0186928 A1 | 8/2007 | Be'Eri |
| 2007/0191697 A1 | 8/2007 | Lynn et al. |
| 2007/0191787 A1 | 8/2007 | Lim et al. |
| 2007/0193579 A1 | 8/2007 | Duquette et al. |
| 2007/0199566 A1 | 8/2007 | Be'eri |
| 2007/0203448 A1 | 8/2007 | Melker et al. |
| 2007/0208267 A1 | 9/2007 | Schmid et al. |
| 2007/0208438 A1 | 9/2007 | El-Mankabady et al. |
| 2007/0215155 A1 | 9/2007 | Marx et al. |
| 2007/0221222 A1 | 9/2007 | Lurie |
| 2007/0225574 A1 | 9/2007 | Ueda |
| 2007/0225623 A1 | 9/2007 | Freeman |
| 2007/0227537 A1 | 10/2007 | Bemister et al. |
| 2007/0227538 A1 | 10/2007 | Scholler et al. |

(56) References Cited

U.S. PATENT DOCUMENTS

| | | |
|---|---|---|
| 2007/0227539 A1 | 10/2007 | Schwaibold et al. |
| 2007/0232951 A1 | 10/2007 | Euliano et al. |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0267015 A1 | 11/2007 | Thoemmes et al. |
| 2007/0271122 A1 | 11/2007 | Zaleski |
| 2007/0272241 A1 | 11/2007 | Sanborn et al. |
| 2007/0272242 A1 | 11/2007 | Sanborn et al. |
| 2007/0272243 A1 | 11/2007 | Sherman et al. |
| 2007/0273216 A1 | 11/2007 | Farbarik |
| 2007/0276439 A1 | 11/2007 | Miesel et al. |
| 2007/0277825 A1 | 12/2007 | Bordewick et al. |
| 2007/0284361 A1 | 12/2007 | Nadjafizadeh et al. |
| 2007/0293741 A1 | 12/2007 | Bardy |
| 2008/0000471 A1 | 1/2008 | Bolam et al. |
| 2008/0000475 A1 | 1/2008 | Hill |
| 2008/0000477 A1 | 1/2008 | Huster et al. |
| 2008/0000478 A1 | 1/2008 | Matthiessen et al. |
| 2008/0000479 A1 | 1/2008 | Elaz et al. |
| 2008/0011294 A1 | 1/2008 | Heesch et al. |
| 2008/0011301 A1 | 1/2008 | Qian |
| 2008/0017189 A1 | 1/2008 | Ruckdeschel et al. |
| 2008/0017198 A1 | 1/2008 | Ivri |
| 2008/0029096 A1 | 2/2008 | Kollmeyer et al. |
| 2008/0029097 A1 | 2/2008 | Schatzl |
| 2008/0033304 A1 | 2/2008 | Dalal et al. |
| 2008/0033661 A1 | 2/2008 | Syroid et al. |
| 2008/0035145 A1 | 2/2008 | Adams et al. |
| 2008/0035146 A1 | 2/2008 | Crabb |
| 2008/0039735 A1 | 2/2008 | Hickerson |
| 2008/0041380 A1 | 2/2008 | Wallace et al. |
| 2008/0041382 A1 | 2/2008 | Matthews et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0053441 A1 | 3/2008 | Gottlib et al. |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |
| 2008/0076970 A1 | 3/2008 | Foulis et al. |
| 2008/0077033 A1 | 3/2008 | Figueiredo et al. |
| 2008/0077038 A1 | 3/2008 | McDonough et al. |
| 2008/0078390 A1 | 4/2008 | Milne et al. |
| 2008/0083644 A1 | 4/2008 | Janbakhsh et al. |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0115786 A1 | 5/2008 | Sinderby et al. |
| 2008/0125828 A1 | 5/2008 | Ignagni et al. |
| 2008/0125873 A1 | 5/2008 | Payne et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0161653 A1 | 7/2008 | Lin et al. |
| 2008/0163872 A1 | 7/2008 | Negele et al. |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0183095 A1 | 7/2008 | Austin et al. |
| 2008/0185009 A1 | 8/2008 | Chonchoias et al. |
| 2008/0208012 A1 | 8/2008 | Ali |
| 2008/0214947 A1 | 9/2008 | Hunt et al. |
| 2008/0216833 A1 | 9/2008 | Pujol et al. |
| 2008/0216835 A1 | 9/2008 | McGinnis et al. |
| 2008/0230057 A1 | 9/2008 | Sutherland |
| 2008/0230065 A1 | 9/2008 | Heinonen |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0251078 A1 | 10/2008 | Buckley et al. |
| 2008/0255880 A1 | 10/2008 | Beller et al. |
| 2008/0257337 A1 | 10/2008 | Denyer et al. |
| 2008/0270912 A1 | 10/2008 | Booth |
| 2008/0275513 A1 | 11/2008 | Lattner et al. |
| 2008/0276939 A1 | 11/2008 | Tiedje |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0293025 A1 | 11/2008 | Zamierowsi et al. |
| 2008/0294060 A1 | 11/2008 | Haro et al. |
| 2008/0295830 A1 | 12/2008 | Martonen et al. |
| 2008/0295839 A1 | 12/2008 | Habashi |
| 2008/0295840 A1 | 12/2008 | Glaw |
| 2008/0306351 A1 | 12/2008 | Izumi |
| 2008/0308105 A1 | 12/2008 | Alder et al. |
| 2008/0308109 A1 | 12/2008 | Brain |
| 2008/0312954 A1 | 12/2008 | Ullrich et al. |
| 2008/0314385 A1 | 12/2008 | Brunner et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0013999 A1 | 1/2009 | Bassin |
| 2009/0038921 A1 | 2/2009 | Kaps et al. |
| 2009/0054743 A1 | 2/2009 | Stewart |
| 2009/0056709 A1 | 3/2009 | Worsoff |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0078258 A1 | 3/2009 | Bowman et al. |
| 2009/0107502 A1 | 4/2009 | Younes |
| 2009/0120439 A1 | 5/2009 | Goebel |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0139522 A1 | 6/2009 | Thomson et al. |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0188502 A1 | 7/2009 | Tiedje |
| 2009/0192421 A1 | 7/2009 | Huster et al. |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0240523 A1 | 9/2009 | Friedlander et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0259135 A1 | 10/2009 | Stasz |
| 2009/0301486 A1 | 12/2009 | Masic |
| 2009/0301487 A1 | 12/2009 | Masic |
| 2009/0301490 A1 | 12/2009 | Masic |

(56) References Cited

U.S. PATENT DOCUMENTS

| | | |
|---|---|---|
| 2009/0301491 A1 | 12/2009 | Masic et al. |
| 2009/0308394 A1 | 12/2009 | Levi |
| 2010/0004517 A1 | 1/2010 | Bryenton et al. |
| 2010/0008466 A1 | 1/2010 | Balakin |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van der Zande et al. |
| 2010/0078017 A1 | 4/2010 | Andrieux et al. |
| 2010/0078019 A1 | 4/2010 | Rittner et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0116270 A1 | 5/2010 | Edwards et al. |
| 2010/0125227 A1 | 5/2010 | Bird |
| 2010/0130873 A1 | 5/2010 | Yuen et al. |
| 2010/0139660 A1 | 6/2010 | Adahan |
| 2010/0145165 A1 | 6/2010 | Merry |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0198289 A1 | 8/2010 | Kameli et al. |
| 2010/0212675 A1 | 8/2010 | Walling et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222693 A1 | 9/2010 | Eriksen et al. |
| 2010/0229863 A1 | 9/2010 | Enk |
| 2010/0236551 A1 | 9/2010 | Enk |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0262035 A1 | 10/2010 | Subramanian |
| 2010/0263669 A1 | 10/2010 | Bowsher |
| 2010/0274100 A1 | 10/2010 | Behar et al. |
| 2010/0282251 A1 | 11/2010 | Calluaud et al. |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2010/0324438 A1 | 12/2010 | Ni et al. |
| 2010/0331715 A1 | 12/2010 | Addison et al. |
| 2011/0004489 A1 | 1/2011 | Schoenberg et al. |
| 2011/0009746 A1 | 1/2011 | Tran et al. |
| 2011/0009763 A1 | 1/2011 | Levitsky et al. |
| 2011/0011400 A1 | 1/2011 | Gentner et al. |
| 2011/0011403 A1 | 1/2011 | Hannah et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041847 A1 | 2/2011 | Cosic |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0067698 A1 | 3/2011 | Zheng et al. |
| 2011/0092839 A1 | 4/2011 | Alshaer et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0208082 A1 | 8/2011 | Madaus et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0265793 A1 | 11/2011 | Haven |
| 2011/0271960 A1 | 11/2011 | Milne et al. |
| 2011/0273299 A1 | 11/2011 | Milne et al. |
| 2011/0288431 A1 | 11/2011 | Alshaer et al. |
| 2011/0313263 A1 | 12/2011 | Wood et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0016252 A1 | 1/2012 | Melker et al. |
| 2012/0029317 A1 | 2/2012 | Doyle et al. |
| 2012/0029362 A1 | 2/2012 | Patangay et al. |
| 2012/0030611 A1 | 2/2012 | Skidmore |
| 2012/0037159 A1 | 2/2012 | Mulqueeny et al. |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0101399 A1 | 4/2012 | Henderson |
| 2012/0123219 A1 | 5/2012 | Georgiev et al. |
| 2012/0133519 A1 | 5/2012 | Milne et al. |
| 2012/0136222 A1 | 5/2012 | Doyle et al. |
| 2012/0136270 A1 | 5/2012 | Leuthardt et al. |
| 2012/0137249 A1 | 5/2012 | Milne et al. |

(56) References Cited

U.S. PATENT DOCUMENTS

| | | |
|---|---|---|
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2018/0304034 A1 | 10/2018 | Vicario et al. |

FOREIGN PATENT DOCUMENTS

| | | |
|---|---|---|
| EP | 1005829 | 6/2000 |
| EP | 1005830 | 6/2000 |
| EP | 1103279 | 5/2001 |
| EP | 996358 | 1/2002 |
| EP | 1277435 | 1/2003 |
| EP | 1421966 | 5/2004 |
| EP | 1464357 | 10/2004 |
| GB | 2319967 | 6/1998 |
| WO | WO 9014852 | 12/1990 |
| WO | WO 9308534 | 4/1993 |
| WO | WO 9312823 | 7/1993 |
| WO | WO 9314696 | 8/1993 |
| WO | WO 9414374 | 7/1994 |
| WO | WO 9508471 | 3/1995 |
| WO | WO 9532480 | 11/1995 |
| WO | WO 9624285 | 8/1996 |
| WO | WO 9706844 | 2/1997 |
| WO | WO 9720592 | 6/1997 |
| WO | WO 9811840 | 3/1998 |
| WO | WO 9814116 | 4/1998 |
| WO | WO 9829790 | 7/1998 |
| WO | WO 9833554 | 8/1998 |
| WO | WO 9840014 | 9/1998 |
| WO | WO 9841267 | 9/1998 |
| WO | WO 9841269 | 9/1998 |
| WO | WO 9841270 | 9/1998 |
| WO | WO 9841271 | 9/1998 |
| WO | WO 9858219 | 12/1998 |
| WO | WO 9903524 | 1/1999 |
| WO | WO 9952431 | 10/1999 |
| WO | WO 9952437 | 10/1999 |
| WO | WO 9959460 | 11/1999 |
| WO | WO 9962403 | 12/1999 |
| WO | WO 0018293 | 4/2000 |
| WO | WO 0019886 | 4/2000 |
| WO | WO 0062664 | 10/2000 |
| WO | WO 0100264 | 1/2001 |
| WO | WO 0100265 | 1/2001 |
| WO | WO 0128416 | 4/2001 |
| WO | WO 0134022 | 5/2001 |
| WO | WO 0245566 | 6/2002 |
| WO | WO 02082967 | 10/2002 |
| WO | WO 03015005 | 2/2003 |
| WO | WO 03024317 | 3/2003 |
| WO | WO 03045493 | 6/2003 |
| WO | WO 03053503 | 7/2003 |
| WO | WO 03060650 | 7/2003 |
| WO | WO 03060651 | 7/2003 |
| WO | WO 03075989 | 9/2003 |
| WO | WO 03075990 | 9/2003 |
| WO | WO 03075991 | 9/2003 |
| WO | WO 03084405 | 10/2003 |
| WO | WO 04014216 | 2/2004 |
| WO | WO 04014226 | 2/2004 |
| WO | WO 04019766 | 3/2004 |
| WO | WO 04032719 | 4/2004 |
| WO | WO 04043254 | 5/2004 |
| WO | WO 2005010796 | 2/2005 |
| WO | WO 05024729 | 3/2005 |
| WO | WO 05055825 | 6/2005 |
| WO | WO 05056087 | 6/2005 |
| WO | WO 05069740 | 8/2005 |
| WO | WO 05077260 | 8/2005 |
| WO | WO 05112739 | 12/2005 |
| WO | WO 06008745 | 1/2006 |
| WO | WO 06009830 | 1/2006 |
| WO | WO 06037184 | 4/2006 |
| WO | WO 06050388 | 5/2006 |
| WO | WO 06051466 | 5/2006 |
| WO | WO 06078432 | 7/2006 |
| WO | WO 06079152 | 8/2006 |
| WO | WO 06094055 | 9/2006 |
| WO | WO 06096080 | 9/2006 |
| WO | WO 06109072 | 10/2006 |
| WO | WO 06123956 | 11/2006 |
| WO | WO 06125986 | 11/2006 |
| WO | WO 06125987 | 11/2006 |
| WO | WO 06125989 | 11/2006 |
| WO | WO 06125990 | 11/2006 |
| WO | WO 06137067 | 12/2006 |
| WO | WO 2007033050 | 3/2007 |
| WO | WO 2007106804 | 9/2007 |
| WO | WO 07145948 | 12/2007 |
| WO | WO 2008008659 | 1/2008 |
| WO | WO 2008021222 | 2/2008 |
| WO | WO 2008030091 | 3/2008 |
| WO | WO 2008042699 | 4/2008 |
| WO | WO 2008058997 | 5/2008 |
| WO | WO 2008062554 | 5/2008 |
| WO | WO 2008113410 | 9/2008 |
| WO | WO 2008113752 | 9/2008 |
| WO | WO 2008118951 | 10/2008 |
| WO | WO 2008140528 | 11/2008 |
| WO | WO 2008146264 | 12/2008 |
| WO | WO 2008148134 | 12/2008 |
| WO | WO 2009024967 | 2/2009 |
| WO | WO 2009027864 | 3/2009 |
| WO | WO 2009036334 | 3/2009 |
| WO | WO 2009060330 | 5/2009 |
| WO | WO 2009124297 | 10/2009 |
| WO | WO 2010009531 | 1/2010 |
| WO | WO 2010020980 | 2/2010 |
| WO | WO 2010021730 | 2/2010 |
| WO | WO 2010039989 | 4/2010 |
| WO | WO 2010126916 | 11/2010 |
| WO | WO 2010141415 | 12/2010 |
| WO | WO 2011005953 | 1/2011 |
| WO | WO 2011022242 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.

(56) References Cited

OTHER PUBLICATIONS

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Boitano, Louis J., "An Evaluation of Home Volume Ventilators That Support OpenCircuit Mouthpiece Ventilation", Respiratory Care, Nov. 2005, vol. 50, No. 11, pp. 1457-1461.

Colombo, Davide et al., "Efficacy of Ventilator Waveforms Observation in Detecting Patient-Ventilator Asychrony", Crit. Care Med., 2011, vol. 39, No. 11, pp. 1-6.

De Wit, M. et al., "Ineffective triggering predicts increased duration of mechanical ventilation", Covidien Clinical Summary of article in Crit Care Med. 2009;37(10):2740-2745, 2 pgs.

De Wit, Marjolein et al., "Ineffective triggering predicts increased duration of mechanical ventilation", Crit. Care Med., 2009 Vol. 37, No. 10, pp. 2740-2745.

PCT International Search Report re: PCT/US09/046409 dated Sep. 29, 2009, 5 pgs.

U.S. Appl. No. 12/980,583, filed Dec. 19, 2010, entitled "Systems And Methods For Ventilation To Obtain A Predetermined Patient Effort", 48 pgs.

SYSTEMS AND METHODS FOR MISSED BREATH DETECTION AND INDICATION

CROSS-REFERENCE TO RELATED APPLICATIONS

This application is a continuation application of U.S. patent application Ser. No. 13/544,462, entitled "SYSTEMS AND METHODS FOR MISSED BREATH DETECTION AND INDICATION," filed on Jul. 9, 2012, the entire disclosure of which is hereby incorporated herein by reference.

INTRODUCTION

A ventilator is a device that mechanically helps patients breathe by replacing some or all of the muscular effort required to inflate and deflate the lungs. During respiration, the ventilator may be configured to present various graphs, charts, and other displays indicative of the physical condition of the patient and the respiratory treatment provided. The ventilatory displays may be further designed to present relevant clinical information to a practitioner in an efficient and orderly manner.

MISSED BREATH DETECTION AND INDICATION

This disclosure describes improved systems and methods for displaying respiratory data to a clinician in a ventilatory system. Respiratory data may be displayed by any number of suitable means, for example, via appropriate graphs, diagrams, charts, waveforms, and other graphic displays. The disclosure describes novel systems and methods for determining and displaying ineffective patient inspiratory or expiratory efforts or missed breaths in a manner easily deciphered by a clinician.

In part, this disclosure describes a method for determining missed breaths. The method includes:
 a) monitoring respiratory data with at least one sensor;
 b) analyzing the respiratory data with a first trigger detection application and a second trigger detection application;
 c) detecting patient inspiratory efforts with the first trigger detection application and the second trigger detection application;
 d) calculating a missed breaths metric based on detected patient inspiratory efforts by the first trigger detection application and detected patient inspiratory efforts by the second trigger detection application; and
 e) displaying a missed breath indicator based on the missed breaths metric.

Yet another aspect of this disclosure describes a medical ventilator including:
 a) at least one display device;
 b) a missed breath module that determines missed breaths based on a first trigger detection application;
 c) a ventilation module that determines ventilation of a patient based on a second trigger detection application; and
 d) at least one memory, communicatively coupled to the at least one processor and containing instructions that, when executed by a processor of the ventilatory system, provide a graphical user interface on the at least one display, comprising a missed breath indicator.

The disclosure further describes a computer-readable medium having computer-executable instructions for performing a method implemented by a ventilator for determining missed breaths, the method includes:
 a) repeatedly monitoring respiratory data with at least one sensor;
 b) repeatedly analyzing the respiratory data with a first trigger detection application and a second trigger detection application;
 c) repeatedly detecting patient inspiratory efforts with the first trigger detection application and the second trigger detection application;
 d) repeatedly calculating a missed breaths metric based on the results of the detection operation; and
 e) repeatedly displaying a missed breath indicator based on the missed breaths metric.

The disclosure also describes a medical ventilator system, including means for monitoring respiratory data with at least one sensor, means for analyzing the respiratory data with a first trigger detection application and a second trigger detection application, means for detecting patient inspiratory efforts with the first trigger detection application and the second trigger detection application, means for calculating a missed breaths metric based on the results of the detection operation, and means for displaying a missed breath indicator based on the missed breaths metric.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments, systems, and methods described below and are not meant to limit the scope of the invention in any manner, which scope shall be based on the claims appended hereto.

DETAILED DESCRIPTION

Figure 1:
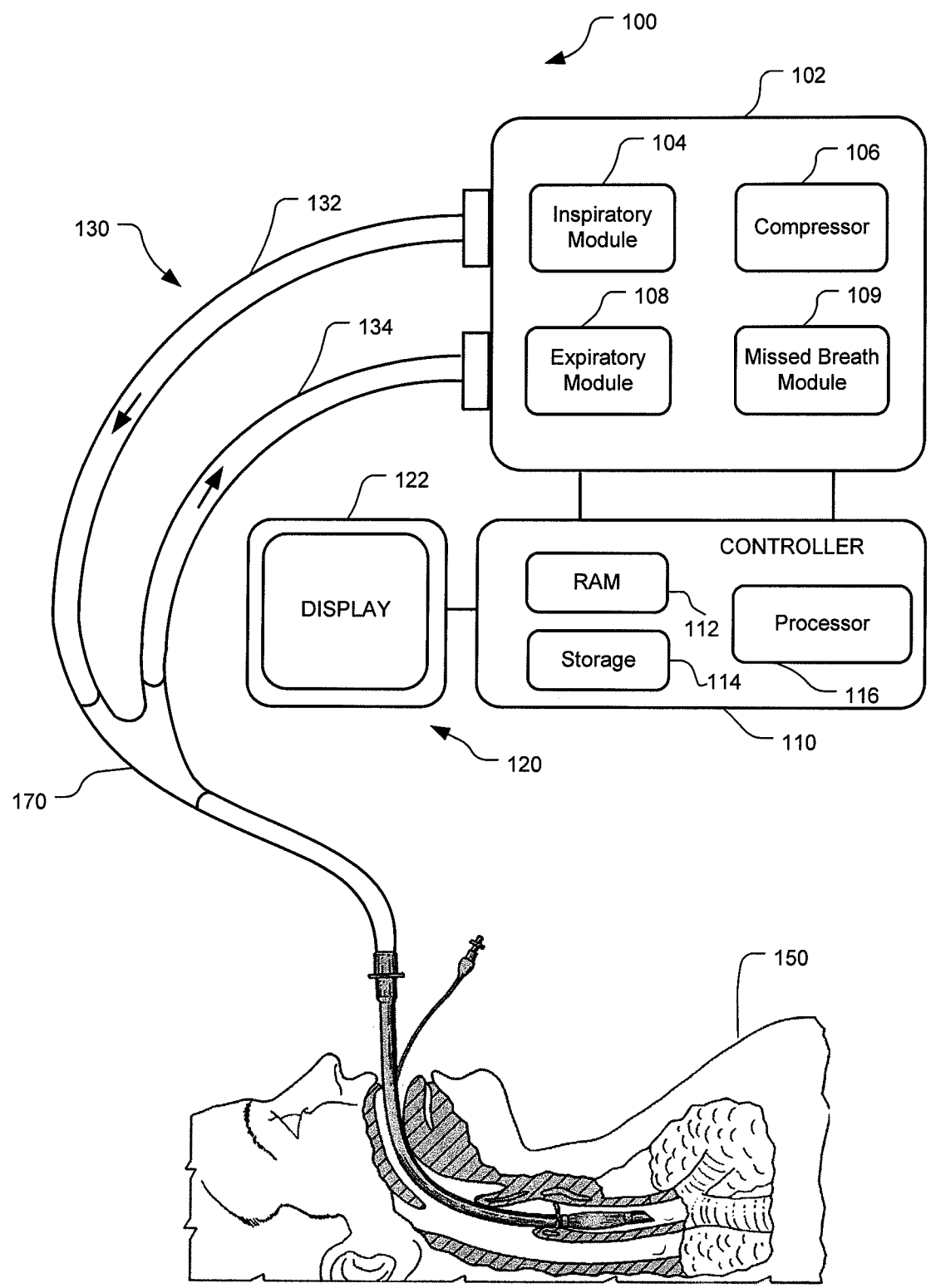
FIG. 1 is a diagram illustrating an embodiment of an exemplary ventilator connected to a human patient.

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients, general gas transport systems, and other therapeutic equipment having graphical user interfaces for displaying data.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

In the medical device field, "patient effort" is a term that can be used to describe many different patient parameters. To be clear, for the purposes of this document, the term "patient effort" shall be used herein to mean a patient's spontaneous attempt to initiate an inspiration or an exhalation as determined by an analysis of pressure, flow, volume, etc. measured by the ventilator. For example, a drop in pressure of greater than a threshold amount may be detected and identified as a single effort of the patient to initiate an inspiration. At time, the phrase "patient inspiratory effort" or "patient expiratory effort" will be used instead of patient effort to remind the reader that what is meant is an attempt by the patient to change the phase of respiratory cycle.

A recent study suggests that clinicians are able to detect less than one-third of patient efforts that do not result in the delivery of a breath, or missed breaths.[1] Further, this study has shown that the rate of correct detection decreases as the prevalence of missed breaths increases. Considering that missed breaths may occur in up to 80% of mechanically ventilated patients, systems and methods for displaying missed breaths are needed. While operating a ventilator on a spontaneously breathing patient, it is desirable to limit, or preferably eliminate, patient efforts that do not result in the delivery of a breath. Hereinafter, patient efforts that do not result in the delivery of a breath shall be referred to as "ineffective patient efforts" or "ineffective triggers". In addition, patient inspiratory efforts that do not result in the delivery of a breath by the ventilator may also be referred to as "missed breaths".

[1] Colombo, D., Cammarota, G., Alemani, M., Carenzo, L., Barra, F., Vaschetto, R., et al. (2011). Efficacy of ventilator waveforms observation in detecting patient-ventilator asynchrony. *Critical Care Medicine*, p. 3.

This disclosure describes systems and methods for displaying respiratory data to a clinician in a ventilatory system. Specifically, the systems and methods disclosed herein determine and/or display ineffective patient efforts.

FIG. 1 is a diagram illustrating an embodiment of an exemplary ventilator 100 connected to a human patient 150. The ventilator 100 includes a pneumatic system 102 (also referred to as a pressure generating system 102) for circulating breathing gases to and from the patient 150 via a ventilation tubing system 130, which couples the patient to the pneumatic system via an invasive patient interface.

The ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

The pneumatic system 102 may be configured in a variety of ways. In the present example, the system 102 includes an expiratory module 108 coupled with the expiratory limb 134 and an inspiratory module 104 coupled with the inspiratory limb 132. A compressor 106 or other source(s) of pressurized gases (e.g., air, oxygen, and/or helium) is coupled with an inspiratory module 104 to provide a gas source for ventilatory support via the inspiratory limb 132. A missed breath module 109 is coupled with the inspiratory module 104 and the expiratory module 108 to detect when a missed breath occurs and is described in more detail in FIG. 2 below.

The pneumatic system 102 may include a variety of other components, including sources for pressurized air and/or oxygen, mixing modules, valves, sensors, tubing, accumulators, filters, etc. A controller 110 is operatively coupled with the pneumatic system 102, signal measurement and acquisition systems, and an operator interface 120 that may enable an operator to interact with the ventilator 100 (e.g., change ventilator settings, select operational modes, view monitored parameters, etc.). The controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator 100. The memory may be transitory or non-transitory. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, the controller 110 may monitor the pneumatic system 102 in order to evaluate the condition of the patient and to ensure proper functioning of the ventilator. The specific monitoring may be based on inputs received from the pneumatic system 102 and sensors, operator interface 120, and/or other components of the ventilator. In the depicted example, operator interface includes a display 122 that is touch-sensitive, enabling the display to serve both as an input and output device.

Figure 2:
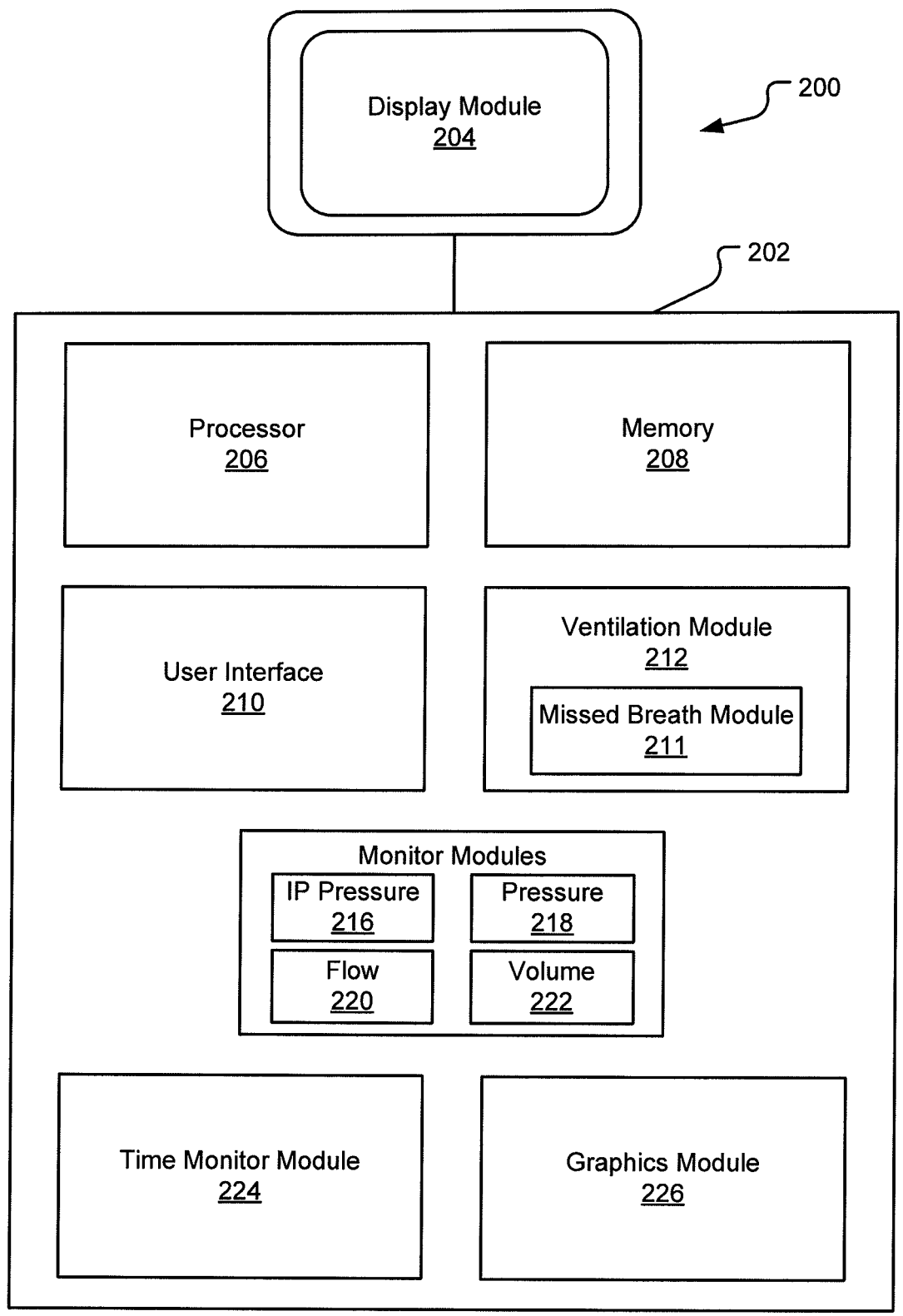
FIG. 2 is a block diagram illustrating an embodiment of a ventilatory system having a graphical user interface for displaying respiratory data.

FIG. 2 is a block diagram illustrating an embodiment of a ventilatory system 200 having a graphical user interface for displaying respiratory data.

A ventilator 202 includes a display module 204, memory 208, one or more processors 206, user interface 210, monitor modules 216-222, time monitor module 224, graphics module 226, and ventilation module 212. The ventilation module 212 further includes a missed breath module 211. The missed breath module 211 in system 200 is the same as the missed breath module 109 described in the system 100 above. The memory 208 is defined as described above for the memory 112 in FIG. 1. Similarly, the one or more processors 206 are defined as described above for the one or more processors 116. The processors 206 may further be configured with a clock whereby elapsed time may be monitored by the system 200. Alternatively, a time monitor module 224 may be provided for monitoring time and associating a temporal element with the various data collected by the monitoring modules 216-222.

The ventilation module 212 oversees ventilation delivered to a patient according to the ventilator settings prescribed for the patient. The ventilator settings are determined by a selected or predetermined ventilation mode and/or breath type. The ventilation module 212 delivers pressure and/or volume into a ventilatory circuit (depending on whether the ventilator is configured for pressure or volume controlled delivery), and thereby into a patient's lungs, based on the breath type and/or mode. Spontaneous breath types are referred to herein as "trigger detection applications," since trigger detection applications require detection of patient effort in order to determine when to deliver a breath to the patient. The trigger detection applications include known spontaneous breath types, such as but are not limited to Proportional Assist Ventilation (PAV), Volume Ventilation Plus (VV+), I:E SYNC, Pressure Support (PS), Volume Support (VS), Assist Control (AC), Volume Control (VC), Pressure Control (PC), Airway Pressure Release Ventilation (APRV), Continuous Positive Airway Pressure (CPAP), and BiLevel Positive Airway Pressure (BPAP). As discussed above, the trigger detection applications trigger the delivery of a breath when a patient effort is detected. While the methods for determining patient effort vary based on the trigger detection application used, in some embodiments, the patient effort is determined based on calculations involving monitored pressure and/or monitored flow. The ventilation module 212, and therefore the trigger detection applications, is communicatively coupled to at least one of the monitoring modules 216-222, the display module 204, the memory 208, the processor 206, the user interface 210, the graphics module 226, the time monitor module 224, and any other suitable component and/or module. For example, the trigger detection application may determine when to trigger a breath based on monitored data received from the monitoring modules 216-222.

The ventilation module 212 further includes a missed breath module 211. The missed breath module 211 utilizes a trigger detection application that detects patient efforts to determine when a patient desires a delivered breath. However, this trigger detection application does not ever actually deliver any breath based on the detected patient efforts and is therefore referred to herein as running in the background or as a "background trigger detection application" (also referred to as a first trigger detection application). A trigger detection application utilized to determine when to deliver the breaths to the patient during ventilation by the ventilator is referred to herein as the "active trigger detection application" (also referred to as a second trigger detection application). Accordingly, the background trigger detection application and the active trigger detection application determine a patient effort by monitoring patient parameters from the monitoring modules 216-222. In some embodiments, the background trigger detection application determines patient efforts based on monitored intrapleural pressure received from the intrapleural pressure (IP) monitoring module 216.

The missed breath module 211 compares the detected patient efforts to the delivered breaths by the ventilation module 212. For any detected patient effort that does not correlate with a delivered breath, the missed breath module 211 determines that the detected patient effort is an ineffective trigger effort by the patient. The missed breath module 211 may store determined information or send determined information to the display module 204, the processor 206, the memory 208, the user interface 210, the time monitor module 224, the graphics module 226, and/or any other suitable component and/or module. The determined information may include a single instance of an ineffective trigger effort by the patient, a sequential history of ineffective trigger efforts over a period of time (either predetermined or input by the clinician), or a rate of ineffective trigger efforts (for example the number of ineffective trigger efforts per minute) that may be averaged over a period of time that is predetermined or input by the clinician.

Further, for any detected patient effort that does correlate with a delivered breath, the missed breath module 211 determines the detected patient effort to be an effective trigger effort by the patient. The missed breath module 211 may store determined information or send determined information to the display module 204, the processor 206, the memory 208, the user interface 210, the time monitor module 224, the graphics module 226, and/or any other suitable component and/or module. The determined information may include a single instance of an effective trigger effort by the patient, a sequential history of effective trigger efforts over a period of time (either predetermined or input by the clinician), or a rate of effective trigger efforts (for example the number of effective trigger efforts per minute) that may be averaged over a period of time that is predetermined or input by the clinician.

The use of intrapleural pressure is an effective way to determine patient effort. When a patient makes an effort to breath, the patient's diaphragm will contract, and decrease the intrapleural pressure in order to draw air (or another substance) into the lungs. Because the contraction of the diaphragm is the effect of patient effort the intrapleural pressure change is the first and most direct way to determine patient effort, as a pressure/flow change will happen subsequently. Therefore a trigger detection application that uses intrapleural pressure is more sensitive to patient efforts than a trigger detection application that only uses pressure or flow. A trigger detection application running in the background is a good way to determine when missed breaths occur due to its inherent sensitivity.

A patient effort may be used to trigger one or more actions on the part of the ventilator, such as but not limited to a transition from exhalation to inhalation (or from inhalation to exhalation). It should be noted that ventilators depending on their mode of operation, may trigger automatically and/or in response to a detected change in a monitored parameter such as but not limited to patient effort, pressure, and flow. In one embodiment a monitored flow signal is used to determine when patient effort occurs. A variety of signals, for example, can be used by a trigger detection application to determine when patient effort occurs such as but not limited to patient airway pressure, lung flow, and intrapleural pressure. In an exemplary embodiment, the ventilator utilizes multiple trigger detection applications simultaneously. A first trigger detection application is used to detect when patient effort occurs, but the ventilator does not actively use the detected patient effort to trigger one or more actions on the part of the ventilator. In this embodiment the first trigger detection application is used to determine when a missed breath occurs. As used herein, the term "missed breath" refers to a patient effort that does not trigger one or more actions on the part of the ventilator, such as the delivery of a breath, the transition from inhalation to exhalation, or the transition from exhalation to inhalation. The first trigger detection application uses intrapleural pressure to detect when a patient effort occurs. In this embodiment, a second trigger detection application is used to determine when to trigger the ventilator. The second trigger detection application may use any suitable current or future known triggering methods based on monitored respiratory parameters such as but not limited to pressure and flow.

The display module 204 presents various input screens to a clinician, including but not limited to one or more graphics display screens, as will be described further herein, for receiving clinician input and for displaying useful clinical data to the clinician. The display module 204 is further configured to communicate with the user interface 210. The display module 204 may provide various windows, controls, and display elements to the clinician via a graphical user interface (GUI) for input and interface command operations. Thus, the user interface 210 may accept commands and input through the display module 204. The display module 204 may also provide useful information in the form of various respiratory data regarding the physical condition of a patient and/or the prescribed respiratory treatment. The useful information may be derived by the ventilator 202, based on data gathered from the various monitoring modules 216-222, and the useful information may be displayed to the clinician in the form of graphs, wave representations, pie graphs, text, symbols, prompts, graphics, lights, lines, indicators, or other suitable forms of graphic display. The display module 204 may further be an interactive display, whereby the clinician may both receive and communicate information to the ventilator 202, as by a touch-activated display screen. Alternatively, the user interface 210 may provide other suitable means of communication with the ventilator 202, for instance by a keyboard or other suitable interactive device.

Figure 4:
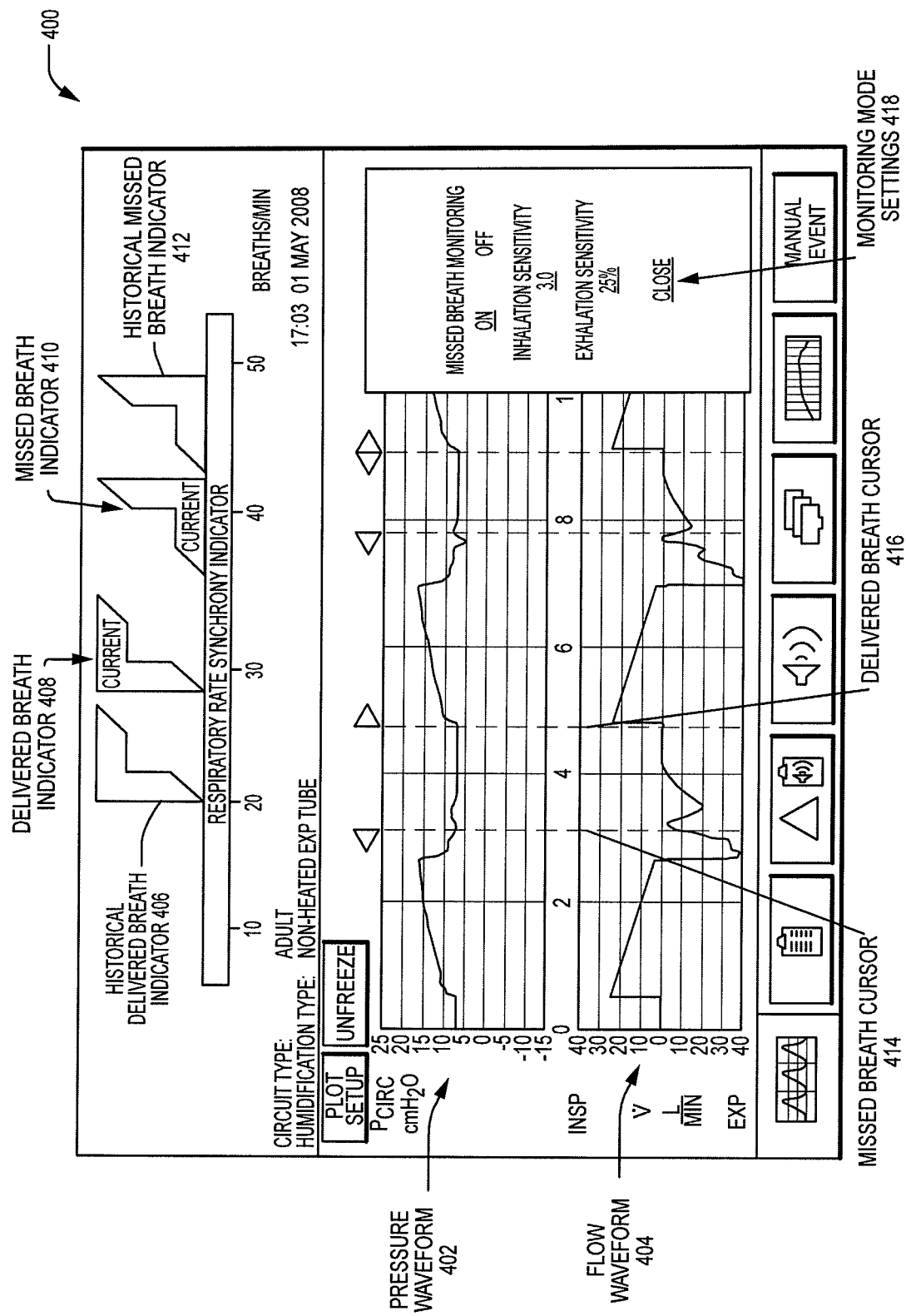
FIG. 4 illustrates an embodiment of a graphical user interface for displaying a plurality of graphical representations of respiratory data, a delivered breath indicator, and a missed breath indicator.

One or more graphics display screens provided by the display module 204 may each display one or more graphic representations of respiratory data, for example, graphical representations may include, inter cilia, pressure waveforms, volume waveforms, flow waveforms, flow curves, pressure-volume loops, flow-volume loops, text, symbols, prompts, graphics, lights, lines, cursors, interactive elements, indicators, or any other current or future known graphical representation suitable for displaying respiratory data. For instance, a volume waveform may depict tidal volume, i.e., the total volume of air inhaled and exhaled for one respiratory cycle, over time. A pressure waveform may depict circuit pressure, as measured or derived, for each inspiration and expiration over time. A pressure-volume loop may be generated for each breath, inspiration represented as a positive curve and expiration represented as a negative curve completing a single loop. In some embodiments the graphical representation is a respiratory rate as illustrated in FIG. 4.

In other embodiments, an indicator is displayed by the one or more graphics display screens provided by the display module 204. The indicator may be a missed breath or a delivered breath indicator. The missed breath indicator displays data relating to a missed breath and the delivered breath indicator displays data relating to a delivered breath. The indicators include as measured or derived, for each instance of a delivered and/or missed breath, for total delivered and/or missed breaths over a period of time, for a rate of delivered and/or missed breaths, for a history of delivered and/or missed breaths, or for any combination thereof. In some embodiments, the indicator is displayed on top of or within the one or more graphical representations.

In some embodiments, the ventilator stores a sequential history of the graphical representations and/or respiratory data, such as a missed breath indicator and a delivered breath indicator. As described above, the graphics module 226, or another suitable component or module, may archive graphical representations and indicators according to time. Some graphical representations and/or indicators may inherently include a time element, as with waveforms of respiratory data presented over time. Other graphical representations or indicators may be presented as a function of a single respiratory cycle, or breath, such as a flow-volume or a pressure-volume loop. The graphics module 226, or another suitable component or module, may associate the respiratory data of the graphical representation and/or indicators with a time element. In the alternative, the monitoring modules 216-222 may associate the respiratory data with a time element, or time stamp, before communicating data to the graphics module 226. In either case, graphical representations and/or indicators may be archived in sequential order based on time. In an embodiment, a cursor or indicator is displayed over a graphical representation of a respiratory signal such as, but not limited to, pressure and flow, at an appropriate temporal location based on when the delivered and/or missed breath occurred.

In an embodiment, a delivered and/or missed breath indicator is displayed as at least one of text, symbol, prompt, graphic, light, line or by another suitable form of graphic display. In another embodiment, the missed breath and delivered breath indicator include the display of a delivered and/or missed breath rate. The graphics module 226, or another suitable component or module, may archive historical data, such as indicators, which may be time-stamped, in sequential order over a particular time period. This rate can be the number or an average of the number of delivered and/or missed breaths per time period, where the time period can be predetermined, such as a minute, or input by the clinician. For example, the indicators may display the number of delivered and/or missed breaths in the last minute. The average can be taken from a predetermined or input number of values over a predetermined or input period of time. For example, the indicators may further display a rate based on an average of the last five values where each value represents the number of delivered and/or missed breaths for that minute. In an embodiment, the indicator may display a percentage or ratio at least partially representative of the delivered and/or missed breaths. For example, if the number of delivered breaths as well as the number of missed breaths are both known, then the indicator may display a percentage or ratio of delivered and/or missed breaths per total breaths, where total breaths is the addition of missed breaths and delivered breaths. In an embodiment, the indicators include a total breath indicator where the total breath indicator represents the addition of missed breaths and delivered breaths. Additionally, an indicator such as but not limited to text, symbol, prompt, graphic, light, line, cursor, interactive element, or indicator may be displayed to represent that missed breaths are being monitored. Further, an indicator such as but not limited to text, symbol, prompt, graphic, light, line, cursor, interactive element, or indicator may be displayed to represent settings for monitoring missed breaths. In some embodiments, a prompt is displayed with adjustable elements representative of turning on and/or off the missed breath module 211 as well as an inhalation and exhalation trigger values for missed breath monitoring. In some embodiments, these indicators are selectable and/or adjusted by a clinician via the user interface.

Data may be collected and displayed according to any suitable method. Thus, a plurality of various graphical representations and/or indicators may be provided, each graphical representation and/or indicator communicating different useful information to the clinician. However, sometimes it may be useful for the clinician to compare the respiratory data displayed if the respiratory data is displayed in a manner that is easier for the clinician to understand, which increases the chance that the clinician will discover a missed breath and can decrease patient-ventilator asynchrony by adjusting ventilator parameters.

The monitoring modules 216-222 operate to monitor the physical condition of the patient in conjunction with the proper operation of the ventilator 202. Although only a sampling of potential monitoring modules are shown and described, any number of suitable monitoring modules may be provided in keeping within the spirit of the present disclosure. The monitoring modules 216-222 may communicate with the display module 204, the user interface 210, the graphics module 226, the missed breath module 211, the ventilation module 212, and/or other suitable modules or processors of the ventilator 202. Specifically, the monitoring modules 216-222 may communicate with the graphics module 226 and/or the display module 204 such that collected data regarding the physical condition of the patient and/or the prescribed ventilation may be displayed to the clinician.

The monitoring modules 216-222 may utilize one or more sensors to detect changes in various physiological parameters. Specifically, the one or more sensors may be placed in any suitable internal location, within the ventilator itself, or in any suitable external location, within the ventilatory circuitry or other devices communicatively coupled to the ventilator 202. For example, sensors may be coupled to inspiratory and/or expiratory modules for detecting changes in, for example, circuit pressure and flow. Additionally, the one or more sensors may be affixed to the ventilatory tubing or may be imbedded in the tubing itself.

An intrapleural pressure monitor module 216 monitors or estimates intrapleural pressure. The term "intrapleural pressure," as used herein, refers generally to the pressure exerted by the patient's diaphragm on the cavity in the thorax that contains the lungs, or the pleural cavity, and should further represent estimates of the pressure and/or any derivatives thereof. The intrapleural pressure monitor module 216 may measure intrapleural pressure according to any suitable method either known or discovered in the future. Alternatively, the intrapleural pressure monitor module 216 may derive intrapleural pressure readings from other data and measurements according to mathematical operations or otherwise. For example, an algorithm that estimates how the patient's intrapleural pressure is changing in real-time based on measured pressure and flow may be used. In one embodiment, the algorithm utilized measured pressure, inlet flow, and outlet flow to determine intrapleural pressure is the algorithm described in U.S. patent application Ser. No. 12/980,583 filed Dec. 29, 2010. U.S. patent application Ser. No. 12/980,583 filed Dec. 29, 2010 is incorporated herein by reference in its entirety.

A pressure monitor module 218 monitors pressure within a ventilatory circuit. The pressure monitor module 218 may measure pressure according to any suitable method either known or discovered in the future. For example, pressure transducers may be attached at various locations along the ventilatory circuit to detect changes in circuit pressure. Specifically, sensors may utilize optical or ultrasound techniques for measuring changes in circuit pressure. Alternatively, the pressure monitor module 218 may derive pressure readings from other data and measurements according to mathematical operations or otherwise.

A flow monitor module 220 monitors airflow within a ventilatory circuit, for example by utilizing sensors as described above for monitoring pressure. Inspiratory flow may be represented as a positive flow and expiratory flow may be represented as a negative flow. Flow may be measured or derived by any suitable method either currently known or disclosed in the future. Specifically, flow may be derived according to mathematical operations or measured at selected points along the ventilatory circuit.

A volume monitor module 222 monitors the volume of air exchanged during a respiratory cycle. The volume monitor module 222 may measure tidal volume by any suitable method, or may derive volume according to mathematical equations based on measurements of pressure and/or flow, for example.

The display module 204 may be further configured to communicate with the graphics module 226. The graphics module 226 may interact with the various monitoring modules 216-222 and may process data received from the monitoring modules 216-222 and the time module 224 to produce the various indicators and/or graphical representations displayed on the display module 204. In some embodiments, the display module 204 further interacts with the missed breath module 109. Alternatively, the graphics module 226 may be configured with a clock for monitoring time without need for an additional time module 224. The graphics module 226 may be configured to process data according to any suitable mathematical or graphical means. For instance, the graphics module 226 may plot raw data received from one monitoring module versus raw data received from another monitoring module. Alternatively, the graphics module 226 may transform raw data received from one or more monitoring modules by utilizing one or more mathematical operations, and may plot the mathematically transformed data versus other raw data, versus other transformed data, or versus a unit of time, for example. The graphics module 226 may transform raw data and may plot transformed or raw data to produce any number of useful graphical representations and/or indicators as may be desired by the clinician. The graphics module 226 may receive commands from the user interface 210 or may be preconfigured to perform certain default operations and manipulations of data for generating useful graphical representations and/or indicators. The graphics module 226 may further be configured to continuously accept data from the various monitoring modules 216-222, the missed breath module 109, and/or from the user interface 210 such that the graphical representations and/or indicators displayed on the display module 204 may be continuously updated and presented in real-time or quasi-real-time to the clinician.

Additionally, the graphics module 226 may be configured to store historical data associated with each graphical representation and/or indicator. The graphics module 226 may be in communication with the time monitor module 224, or other clock feature provided by the ventilator 202, such that data within each graphical representation and/or indicator is associated with a time stamp. Specifically, underlying respiratory data may be time-stamped as it is received from the monitoring modules 216-222. As graphical representations of the respiratory data are generated by the graphics module 226, a time element may be incorporated such that each position on a waveform or loop, for instance, is associated with a time element. The graphics module 226 may archive time-stamped or non-time-stamped historical data in sequential order over a particular time period. Thereafter, a clinician may utilize a scroll feature to scroll through a history of graphical representations and/or indicators stored over the time period. The time period may represent any temporal period of interest to the clinician, for instance, an hour, a day, a week, or an entire treatment period. Indeed, the ventilator may archive all data during a respiratory treatment period unless the clinician instructs otherwise. In the alternative, the ventilator may archive data over a most recent period, perhaps the last day, in order to free memory for other ventilatory functions.

In an embodiment, as a clinician utilizes the scroll feature, the graphics module 226 may drill into the underlying historical data to determine an associated time element, or may retrieve a time element associated with each stored graphical representation and/or indicator, in order to provide an appropriate graphical representation and/or indicators to the clinician based on a selected historical time. For example, the graphics module 226 may determine an appropriate historical pressure waveform, an appropriate historical indicator, and an appropriate position on the appropriate pressure waveform associated with a selected historical time. The graphics module 226 may display a cursor at the appropriate position on the appropriate pressure waveform and may display historical indicators, such as but not limited to missed breath indicators, delivered breath indicators, and total breath indicators, within an appropriate range of the cursor. The graphics module 226 may also be configured to simultaneously display cursors and historical indicators in corresponding locations on any other displayed graphical representations based on the selected historical time. As described above, reference lines intersecting the cursors and the axes of the various graphical representations may also be provided, along with a plurality of boxed fields for highlighting specific respiratory data associated with the selected historical time.

Figure 3:
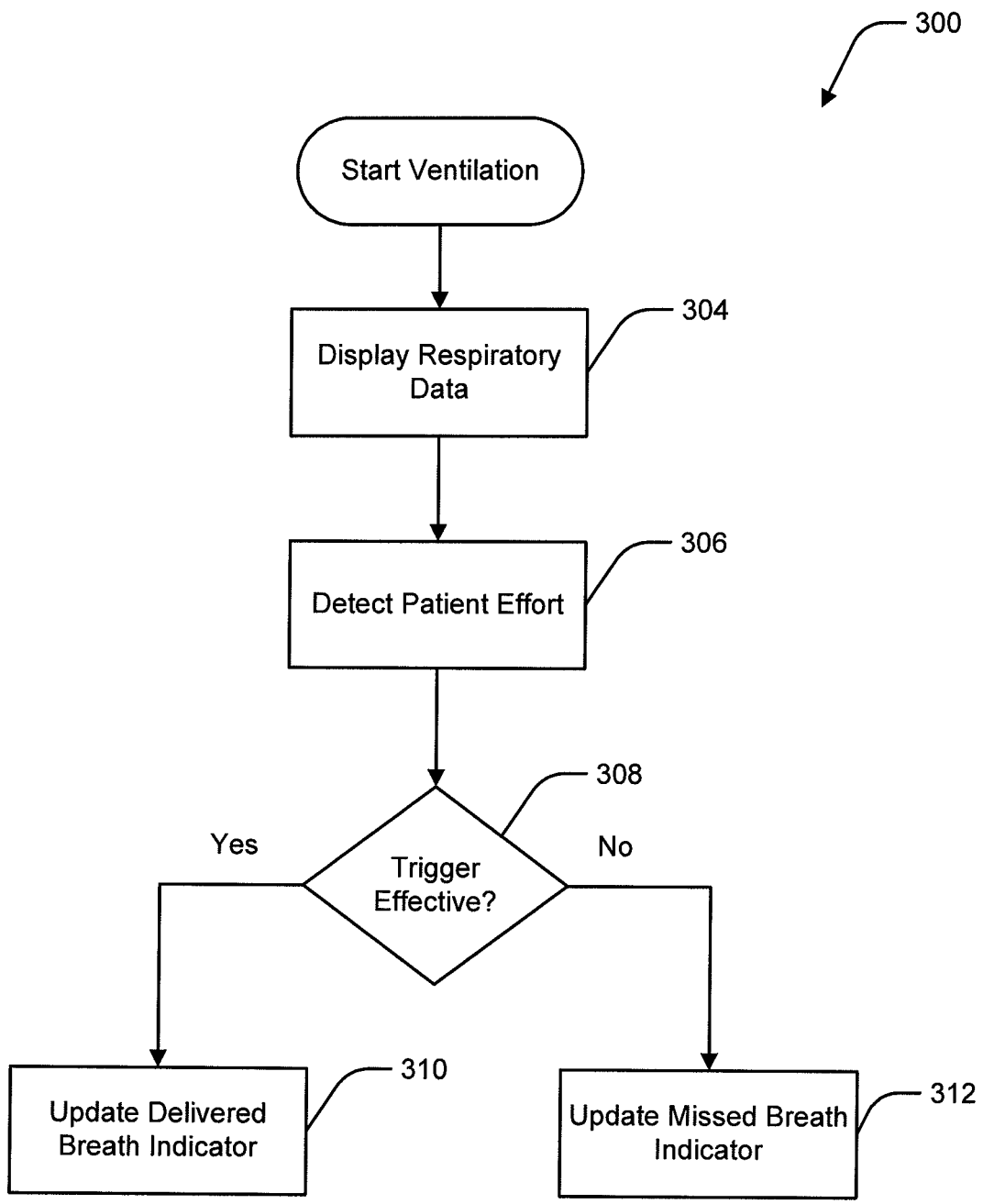
FIG. 3 is a flow diagram illustrating an embodiment of a method for ventilating a patient on a ventilator having a graphical user interface for displaying respiratory data.

FIG. 3 is a flow diagram illustrating an embodiment of a method 300 for ventilating a patient on a ventilator. In some embodiments, the ventilator performing the method 300 is the ventilator 100 described in FIG. 1, having a graphical user interface for displaying respiratory data. The method 300 includes a respiratory data display operation 304, an effort detection operation 306, an effective trigger determination operation 308, an update delivered breath indicator operation 310, and an update missed breath indicator operation 312.

A patient is ventilated with a ventilator. As illustrated, the method 300 begins after the start of ventilation.

The method 300 includes the respiratory data display operation 304. The ventilator system during the respiratory data display operation 304 determines at least one graphical representation of respiratory data based on the ventilation of the patient and displays the graphical representations. In one embodiment, the ventilator uses the display 122 to perform the respiratory data display operation 304. The graphical representations may include a waveform, flow curve, pressure-volume loop, flow-volume loop, text symbol, prompt, graphic, light, line, cursor, interactive element, and indicator. The graphical representation may include collected data regarding the physical condition of the patient. The graphical representation may be displayed to the clinician in real-time, quasi-real-time, or historically. As described above, a ventilator may provide numerous graphical representations of respiratory data to a clinician during respiration of a patient. The graphical representation may be determined by the ventilator during the respiratory data display operation 304 based on monitored data. The ventilator may receive the monitored data from monitoring modules, such as the monitoring modules 216-222 discussed in FIG. 2 above. The ventilator may store a sequential history of the graphical representations provided. The graphics module 226, or another suitable component or module, may archive graphical representations according to time. Some graphical representations may inherently include a time element, as with waveforms of respiratory data presented over time. Other graphical representations may be presented as a function of a single respiratory cycle, or breath, such as a flow-volume or a pressure-volume loop. The graphics module 226, or another suitable component or module, may associate the respiratory data of the graphical representation with a time element. In the alternative, the monitoring modules 216-222 may associate the respiratory data with a time element, or time stamp, before communicating data to the graphics module 226. In either case, graphical representations may be archived in sequential order based on time.

It is understood by a person of skill in the art that the respiratory data display operation 304 may be performed at any time and/or simultaneously with any other operation in the method 300 that is performed after the start of ventilation but before the performance of the display delivered breath indicator operation 310 and the display missed breath indicator operation 312.

The method 300 further includes the effort detection operation 306. The ventilator system during the effort detection operation 306 monitors patient respiratory data and detects patient effort with an active and a background trigger detection application. As used herein, the term "patient effort" refers to an effort exerted by the patient to inspire and/or exhale gases. As discussed above, a trigger detection application is a hardware or software application that determines when a patient effort occurs based on a selected or predetermined spontaneous breath type. The active trigger detection application may include Proportional Assist Ventilation (PAV), Volume Ventilation Plus (VV+), I:E SYNC, Pressure Support (PS), Volume Support (VS), Assist Control (AC), Volume Control (VC), Pressure Control (PC), Airway Pressure Release Ventilation (APRV), Continuous Positive Airway Pressure (CPAP), and BiLevel Positive Airway Pressure (BPAP). The active trigger detection application may determine patient efforts based on monitoring respiratory parameters such as but not limited to pressure and flow. In one embodiment the background trigger detection application is I:E SYNC. In this embodiment, the background trigger detection application determines patient effort based on monitoring intrapleural pressure.

As illustrated, the method 300 includes the trigger determination operation 308. The ventilator during the trigger determination operation 308 determines whether a detected patient effort was effective or ineffective. The effective patient effort is determined based on detected patient effort by the second trigger detection application. In an embodiment, a patient effort detected by the second trigger detection application that results in the delivery of a breath is determined to be effective. In another embodiment, if a first patient effort detected by the first trigger detection application correlates to a second patient effort detected by the second trigger detection application, then the two detected patient efforts are considered to have been generated by the same patient effort and is therefore determined effective. The first patient effort and the second patient effort may correlate if recorded at the same time or within a reasonable and expected time delay, such as 3 seconds or less. This effective patient effort may result in the delivery of a breath.

The ineffective trigger effort is determined based on detected patient effort by the first trigger detection application not correlating with detected patient effort by the second trigger detection application. The first patient effort and the second patient effort may correlate if recorded at the same time or within a reasonable and expected time delay, such as 3 seconds or less. If there is not any correlation between the first detected patient effort and the second detected patient effort, then the patient effort that was not used to trigger the ventilator, in this case the first detected patient effort, is determined to be ineffective. Further, a missed breath is the direct result of an ineffective effort. In an embodiment, an equation or mathematical operation is used to determine if the first detected patient effort correlates with the second detected patient effort. In an embodiment, the first trigger detection application is running in the background, and not actively used to trigger the delivery of breaths to the patient. Further, the second trigger detection application is actively working and is used to trigger the delivery of breaths to the patient. In an embodiment, the first trigger detection application determines patient effort based at least in part on intrapleural pressure.

If the detected patient effort is determined to be effective, the method 300 will perform the update delivered breath indicator operation 310. If the detected patient effort is determined to be ineffective, the method 300 will perform the update missed breath indicator operation 312.

The method 300 further includes the update delivered breath indicator operation 310. The ventilator during the update delivered breath indicator operation 310 displays a delivered breath indicator for the effective trigger effort on the graphical representation. In an embodiment, the ventilator during the update delivered breath indicator operation 310 updates the display of a delivered breath indicator that was previously displayed. The ventilator may store a sequential history of the delivered breath indicators provided. As described above, the graphics module 226, or another suitable component and/or module, may archive delivered breath indicators according to time, and may associate a time element with the delivered breath indicators. In an alternative embodiment, the monitoring modules 216-222 associate the delivered breath indicators with a time element, or time stamp, before communicating data to the graphics module 226. In either case, delivered breath indicators may be archived in sequential order based on time, resulting in an archived effective indicator. In an embodiment, the delivered breath indicator is displayed on top of a graphical representation of a respiratory signal such as, but not limited to, pressure and flow, at an appropriate temporal location based on when the delivered breath occurred. In an embodiment, a delivered breath indicator is displayed as at least one of text, symbol, prompt, graphic, light, line, cursor, interactive element, indicator, or by another suitable form of graphic display. In another embodiment the delivered breath indicator displays a delivered breath rate. This rate can be the number or an average of the number of delivered breaths per time period, where the time period can be predetermined, such as a minute, or input by the clinician. For example, a delivered breath indicator displays the number of delivered breaths in the last minute. The average can be taken from a predetermined or input number of values over a predetermined or input period of time. For example, a delivered breath indicator displays a rate based on an average of the last five values where each value represents the number of delivered breaths for that minute. In an embodiment, a delivered breath indicator displays a percentage or ratio at least partially representative of the delivered breaths. For example, if the number of delivered breaths as well as the number of missed breaths are both known then a delivered breath indicator representing a percentage or ratio of delivered breaths per total breaths may be displayed where total breaths is the addition of missed breaths and delivered breaths. Indeed, data may be collected and displayed according to any suitable method.

The method 300 further includes the update missed breath indicator operation 312. The ventilator during the update missed breath indicator operation 312 displays a missed breath indicator for the ineffective trigger effort on the graphical representation. In an embodiment, the ventilator during the update missed breath indicator operation 312 updates the display of a missed breath indicator that was previously displayed. The ventilator may store a sequential history of the missed breath indicators provided. The missed breath module 211, or another suitable component and/or module, may archive missed breath indicators according to time, and may associate a time element with the missed breath indicators. In the alternative, the monitoring modules 216-222 may associate the missed breath indicators with a time element, or time stamp, before communicating data to the graphics module 226 and/or the missed breath module 211. In either case, missed breath indicators may be archived in sequential order based on time, resulting in an archived ineffective indicator. In an embodiment missed breath indicators as well as delivered breath indicators may be archived in sequential order based on time, resulting in an archived total indicator. In an embodiment, the missed breath indicator is displayed on top of a graphical representation of a respiratory signal such as, but not limited to, pressure and flow, at an appropriate temporal location based on when the missed breath occurred. In an embodiment, a missed breath is displayed as at least one of text, symbol, prompt, graphic, light, line, cursor, interactive element, indicator, or by another suitable form of graphic display. In another embodiment the missed breath indicator displays a missed breath rate. This rate can be the number or an average of the number of missed breaths per time period, where the time period can be predetermined, such as a minute, or input by the clinician. For example, a missed breath indicator displays the number of missed breaths in the last minute. The average can be taken from a predetermined or input number of values over a predetermined or input period of time. For example, a missed breath indicator displays a rate based on an average of the last five values where each value represents the number of missed breaths for that minute. In an embodiment, a missed breath indicator displays a percentage or ratio at least partially representative of the missed breaths. For example, if the number of delivered breaths as well as the number of missed breaths are both known then a missed breath indicator representing a percentage or ratio of missed breaths per total breaths may be displayed where total breaths is the addition of missed breaths and delivered breaths. In an embodiment, the missed breath indicator displays a total breath indicator where the total breath indicator at least partially represents the total breaths, where the total breaths is the addition of missed breaths and delivered breaths. Additionally, a missed breath indicator may be displayed to represent that missed breaths are being monitored. Further, a missed breath indicator may be displayed to represent settings for monitoring missed breaths. For example, a missed breath indicator displays a prompt with adjustable elements representative of turning on and/or off the missed breath monitoring as well as inhalation and exhalation trigger values for missed breath monitoring using the first trigger detection application. Indeed, data may be collected and displayed according to any suitable method.

It is understood by a person of skill in the art that the update delivered breath indicator operation 310 and the update missed breath indicator operation 312 may be performed in any order and/or simultaneously. In one embodiment, the update delivered breath indicator operation 310 and/or the update missed breath indicator operation 312 are performed in real-time or quasi-real-time.

In an embodiment, the method 300 repeats and/or is performed at least once during each breath cycle.

FIG. 4 illustrates an embodiment of a graphical user interface (GUI) 400 for displaying a plurality of graphical representations of respiratory data, a delivered breath indicator, and a missed breath indicator. Specifically, FIG. 4 illustrates an embodiment of a missed breath display screen wherein a clinician may initiate a missed breath monitoring mode and thereafter may simultaneously view a plurality of graphical representations and missed breath indicators corresponding to missed breaths.

The disclosed embodiment of the graphical user interface 400 provides a plurality of graphical representations of respiratory data to a clinician. Graphical representations may include, inter cilia, pressure waveforms, volume waveforms, flow waveforms, flow curves, pressure-volume loops, flow-volume loops, text, symbols, prompts, graphics, lights, lines, cursors, interactive elements, indicators, or any other current or future known graphical representation suitable for the GUI 400. Specifically, the GUI 400 includes, for example, a pressure waveform (graphical representation 402), a flow waveform (graphical representation 404), a historical delivered breath indicator (delivered breath indicator 406), a delivered breath indicator (delivered breath indicator 408), a missed breath indicator (missed breath indicator 410), a historical missed breath indicator (missed breath indicator 412), a missed breath cursor (missed breath indicator 414), a delivered breath cursor (delivered breath indicator 416), and a monitoring mode settings box (missed breath indicator 418).

The pressure waveform 402 may display circuit pressure in cm H$_2$O over time (for example, over seconds, s). As shown, the pressure waveform 402 illustrates two distinct peaks in circuit pressure, corresponding to the inspiratory phases of two respiratory cycles, or breaths. The flow waveform 404 may display flow in liters (L) over time (for example, over minutes, min). As shown, the flow waveform 404 illustrates inspiratory flow as a positive curve, and expiratory flow as a negative curve. Two distinct respiratory cycles or breaths, each including a positive inspiratory phase and a negative expiratory phase, are illustrated in the flow waveform 404.

As described previously, the delivered breath indicator 408 may be provided to display the rate of delivered breaths over time (for example, over minutes, min) for a period of time. As shown, the delivered breath indicator 408 is a floating indicator over an axis of breaths per minute. The delivered breath indicator 408 may be text, symbol, prompt, graphic, light, line, cursor, interactive element, indicator, or any display element suitable to display a rate of delivered breaths over time. In an embodiment, the period of time is predetermined or input by a clinician. For example, if a clinician wants to see the effect of changing settings on patient-ventilator synchrony, the clinician can set the historical delivered breath indicator 406 as the current delivered breath indicator 408. Then the clinician can change ventilation settings and observe how the change in settings affects the delivered breath indicator 408. This observation may give the clinician insight as to how effective the change in ventilation settings was to reduce patient-ventilator asynchrony. In an embodiment, the delivered breath indicator 408 includes a numeric value and/or text used to display delivered breaths over time for a period of time. For example, at least one of a number of delivered breaths over a period of time, such as the last minute, and a percentage or ratio of how many of the total breaths over a period of time, such as the last minute, were delivered where total breaths is the addition of missed breaths and delivered breaths.

As described previously the missed breath indicator 410 may be provided to display the rate of missed breaths over time (for example, over minutes, min) for a period of time. As shown, the missed breath indicator 410 is a floating indicator over an axis of breaths per minute. The missed breath indicator 410 may be text, symbol, prompt, graphic, light, line, cursor, interactive element, indicator, or any display element suitable to display a rate of missed breaths over time. In an embodiment, the period of time is predetermined or input by a clinician. For example, if a clinician wants to see the effect of changing settings on patient-ventilator synchrony, the clinician can set the historical missed breath indicator 412 as the current missed breath indicator 410. Then the clinician can change ventilation settings and observe how the change in settings affects the missed breath indicator 410. This observation may give the clinician insight as to how effective the change in ventilation settings was to reduce patient-ventilator asynchrony. In an embodiment, the missed breath indicator 410 includes a numeric value and/or text used to display missed breaths over time for a period of time. For example, at least one of a number of missed breaths over a period of time, such as the last minute, and a percentage or ratio of how many of the total breaths over a period of time, such as the last minute, were missed where total breaths is the addition of missed breaths and delivered breaths.

As previously described, the historical delivered breath indicator 406 may be provided to display the rate of delivered breaths over time (for example, over minutes, min) for a historical archived period of time. As shown, the historical delivered breath indicator 406 is a floating indicator over an axis of breaths per minute. In an embodiment, the historical archived period of time is predetermined or input by a clinician. For example, if a clinician wants to see the effect of changing settings on patient-ventilator synchrony, the clinician can set the historical delivered breath indicator 406 as the current delivered breath indicator 408. Then the clinician can change ventilation settings and observe how the change in settings affects the delivered breath indicator 408. This observation may give the clinician insight as to how effective the change in ventilation settings was to reduce patient-ventilator asynchrony. In an embodiment, the historical delivered breath indicator 406 includes a numeric value and/or text used to display delivered breaths over time for a historical archived period of time. For example, at least one of a number of delivered breaths over a period of time, such as a minute, and a percentage or ratio of how many of the total breaths over a period of time, such as a minute, were delivered where total breaths is the addition of missed breaths and delivered breaths.

As previously described, the historical missed breath indicator 412 displays the rate of total breaths over time (for example, over minutes, min) for a historical archived period of time, where total breaths is the addition of delivered breaths and missed breaths. In another embodiment, the historical missed breath indicator 412 displays the rate of missed breaths over time (for example, over minutes, min) for a historical archived period of time. As shown, the historical missed breath indicator 412 is a floating indicator over an axis of breaths per minute. Further, the historical missed breath indicator 412 is of a shape that will form a distinguishable shape, which may or may not be different, when representing the same value on the axis as the historical delivered breath indicator 406. In an embodiment, the historical archived period of time is predetermined or input by a clinician. For example, if a clinician wants to see the effect of changing settings on patient-ventilator synchrony, the clinician can set the historical missed breath indicator 412 as the current missed breath indicator 410. Then the clinician can change ventilation settings and observe how the change in settings affects the missed breath indicator 410. This observation may give the clinician insight as to how effective the change in ventilation settings was to reduce patient-ventilator asynchrony. In an embodiment, the historical missed breath indicator 412 includes a numeric value and/or text used to display missed breaths over time for a historical archived period of time. For example, at least one of a number of missed breaths over a period of time, such as a minute, and a percentage or ratio of how many of the total breaths over a period of time, such as a minute, were missed where total breaths is the addition of missed breaths and delivered breaths. It should be noted that in the depicted embodiment the axis label "Respiratory Rate Synchrony Indicator" represents a missed breath indicator used to display that a mode, such as the missed breath module 211 or trigger detection applications as described above, is running in the background to determine when missed breaths occur.

The GUI 400 further includes the missed breath cursor 414. The missed breath cursor 414 is a specific type of missed breath indicator 410 that is provided to display relative to another graphical representation, for example the pressure waveform 402 and/or the flow waveform 404, when a missed breath occurred. As described previously with reference to the graphics module 226, missed breath indicators may be time-stamped, or otherwise associated with a time element, when respiratory data is received by the monitoring modules 216-222 or the missed breath module 211. Alternatively, a time element may be associated with the respiratory data when a graphical representation and/or indicator is generated by the graphics module 226 or missed breath module 211, for example. In either case, when a clinician utilizes a cursor mode to scroll back into historical data, the graphics module 226, or other retrieval module (not shown), may determine appropriate respiratory data corresponding to the scroll time. The appropriate respiratory data may then be displayed as the missed breath cursor 414. As shown, the missed breath cursor 414 is a cursor displayed at the correct temporal location over the pressure waveform 402 and the flow waveform 404, and represents an occurrence of a missed breath. Further, the missed breath cursor 414 as shown is of a shape that will form a distinguishable shape, which may or may not be different, when located at the same or similar temporal location as the delivered breath cursor 416. In an embodiment, a patient effort detected using the missed breath module 211 or the trigger detection applications as described above while running in the background to detect missed breaths is displayed using the missed breath cursor 414. As shown, the most recent breath (the cursor furthest to the right of the pressure 402 and flow waveforms 404) was triggered by a patient effort that was detected by both a mode running in the background to detect missed breaths and a mode used to trigger the ventilator, and therefore the cursor forms a different shape, in this case a diamond as opposed to a triangle, which can be interpreted by a clinician as a synchronous patient effort, or a patient effort that directly resulted in the delivery of a breath from the ventilator.

The GUI 400 further includes the delivered breath cursor 416. The delivered breath cursor 416 is a specific type of missed breath indicator 410 that is provided to display relative to another graphical representation, for example the pressure waveform 402 and/or the flow waveform 404, when a delivered breath occurred. As described previously with reference to the graphics module 226, delivered breath indicators may be time-stamped, or otherwise associated with a time element, when respiratory data is received by the monitoring modules 216-222. Alternatively, a time element may be associated with the respiratory data when a graphical representation is generated by the graphics module 226, for example. In either case, when a clinician utilizes a cursor mode to scroll back into historical data, the graphics module 226, or other retrieval module (not shown), may determine appropriate respiratory data corresponding to the scroll time. The appropriate respiratory data may then be displayed as the delivered breath cursor 416. As shown, the delivered breath cursor 416 is a cursor displayed at the correct temporal location over the pressure waveform 402 and the flow waveform 404, and represents an occurrence of a delivered breath. Further, the delivered breath cursor 416 as shown is of a shape that will form a distinguishable shape, which may or may not be different, when located at the same or similar temporal location as the missed breath cursor 414. In an embodiment, a patient effort detected using the monitoring modules 216-222 or the trigger detection applications as described above while running in the foreground to detect patient effort or other respiratory data used to trigger the delivery of a breath is displayed using the delivered breath cursor 416.

The GUI 400 further includes the monitoring mode settings 418. The monitoring mode settings 418 may be provided to display and/or adjust one or more settings relating to the trigger detection application running in the background to detect missed breaths. As shown the monitoring mode settings 418 include an option for turning the missed breath monitoring on or off, a setting to adjust the inhalation trigger sensitivity level of the background trigger detection application, a setting to adjust the exhalation trigger sensitivity level of the background trigger detection application, and an option to close, or not display, the monitoring mode settings 418.

The disclosed windows and elements of the GUI 400 may be arranged in any suitable order or configuration such that information may be communicated to the clinician in an efficient and orderly manner. Windows disclosed in the illustrated embodiment of the GUI 400 may be configured with elements for accessing alternative graphical display screens as may be provided by the ventilator. Disclosed windows and elements are not to be understood as an exclusive array, as any number of similar suitable windows and elements may be displayed for the clinician within the spirit of the present disclosure. Further, the disclosed windows and elements are not to be understood as a necessary array, as any number of the disclosed windows and elements may be appropriately replaced by other suitable windows and elements without departing from the spirit of the present disclosure. The illustrated embodiment of the GUI 400 is provided as an example only, including potentially useful windows and elements that may be provided to the clinician to facilitate the input of selections and commands relevant to the display of respiratory data and to display such respiratory data in an orderly and informative way, as described herein.

The above-mentioned embodiments of one or more missed breath indicator display screens, illustrated in FIG. 4, are not meant to provide an exclusive array of potential or possible embodiments. Indeed, some of the features and characteristics of the above embodiments may be interchanged and combined to provide additional embodiments and configurations of the described graphical user interfaces. In addition, in keeping with the spirit of the present disclosure, features described may not be essential, but may be added or removed according to the desires and needs of a clinician, hospital, clinic, or other entity or individual.

Figure 5:
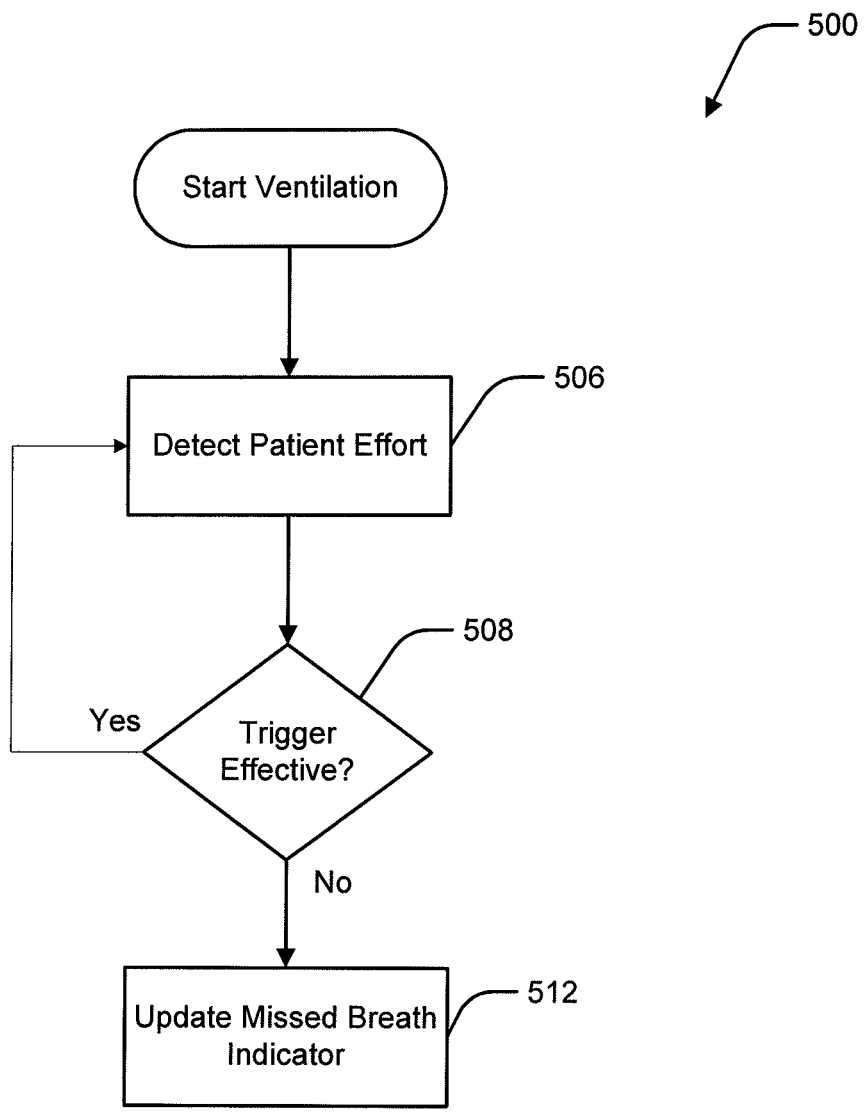
FIG. 5 is a flow diagram illustrating an embodiment of a method for displaying and/or updating the display of a missed breath indicator.

FIG. 5 is a flow diagram illustrating an embodiment of a method 500 for displaying and/or updating the display of a missed breath indicator. In an embodiment, the method 500 is performed by the missed breath module 109 described in FIG. 1. As illustrated, the ventilator system during the method 500 starts ventilation as is described with respect to starting ventilation in the above method 300. The method 500 further includes a detect patient effort operation 506 and an effective trigger determination operation 508, which are the same as operations 306 and 308, respectively, and a update missed breath indicator operation 512. During the effective trigger determination operation 508 if the patient effort is determined to be effective the method 500 will return to the detect patient effort operation 506. During the effective trigger determination operation 508 if the patient effort is determined to be ineffective the method 500 will proceed to the update missed breath indicator operation 512.

The method 500 further includes the update missed breath indicator operation 512. The ventilator during the update missed breath indicator operation 512 displays a missed breath indicator for the ineffective trigger effort. In an embodiment, the ventilator during the update missed breath indicator operation 512 updates the display of a missed breath indicator previously displayed for the ineffective trigger effort. The ventilator may store a sequential history of the missed breath indicators provided. The missed breath module 211, or another suitable component and/or module, may archive missed breath indicators according to time, and may associate a time element with the missed breath indicators. In the alternative, the monitoring modules 216-222 may associate the missed breath indicators with a time element, or time stamp, before communicating data to the graphics module 226 and/or the missed breath module 211. In either case, missed breath indicators may be archived in sequential order based on time, resulting in an archived ineffective indicator. In an embodiment, a missed breath is displayed as at least one of text, symbol, prompt, graphic, light, line, cursor, interactive element, indicator, or by another suitable form of graphic display. In another embodiment the missed breath indicator displays a missed breath rate. This rate can be the number or an average of the number of missed breaths per time period, where the time period can be predetermined, such as a minute, or input by the clinician. For example, a missed breath indicator displays the number of missed breaths in the last minute. The average can be taken from a predetermined or input number of values over a predetermined or input period of time. For example, a missed breath indicator displays a rate based on an average of the last five values where each value represents the number of missed breaths for that minute. In an embodiment, a missed breath indicator displays a percentage or ratio at least partially representative of the missed breaths. For example, if the number of delivered breaths as well as the number of missed breaths are both known then a missed breath indicator representing a percentage or ratio of missed breaths per total breaths may be displayed where total breaths is the addition of missed breaths and delivered breaths. In an embodiment, the missed breath indicator displays a total breath indicator where the total breath indicator at least partially represents the total breaths, where the total breaths are the addition of missed breaths and delivered breaths. Additionally, a missed breath indicator may be displayed to represent that missed breaths are being monitored. Further, a missed breath indicator may be displayed to represent settings for monitoring missed breaths. For example, a missed breath indicator displays a prompt with adjustable elements representative of turning on and/or off the missed breath monitoring as well as inhalation and exhalation trigger values for missed breath monitoring using the first trigger detection application. Indeed, data may be collected and displayed according to any suitable method.

Figure 6:
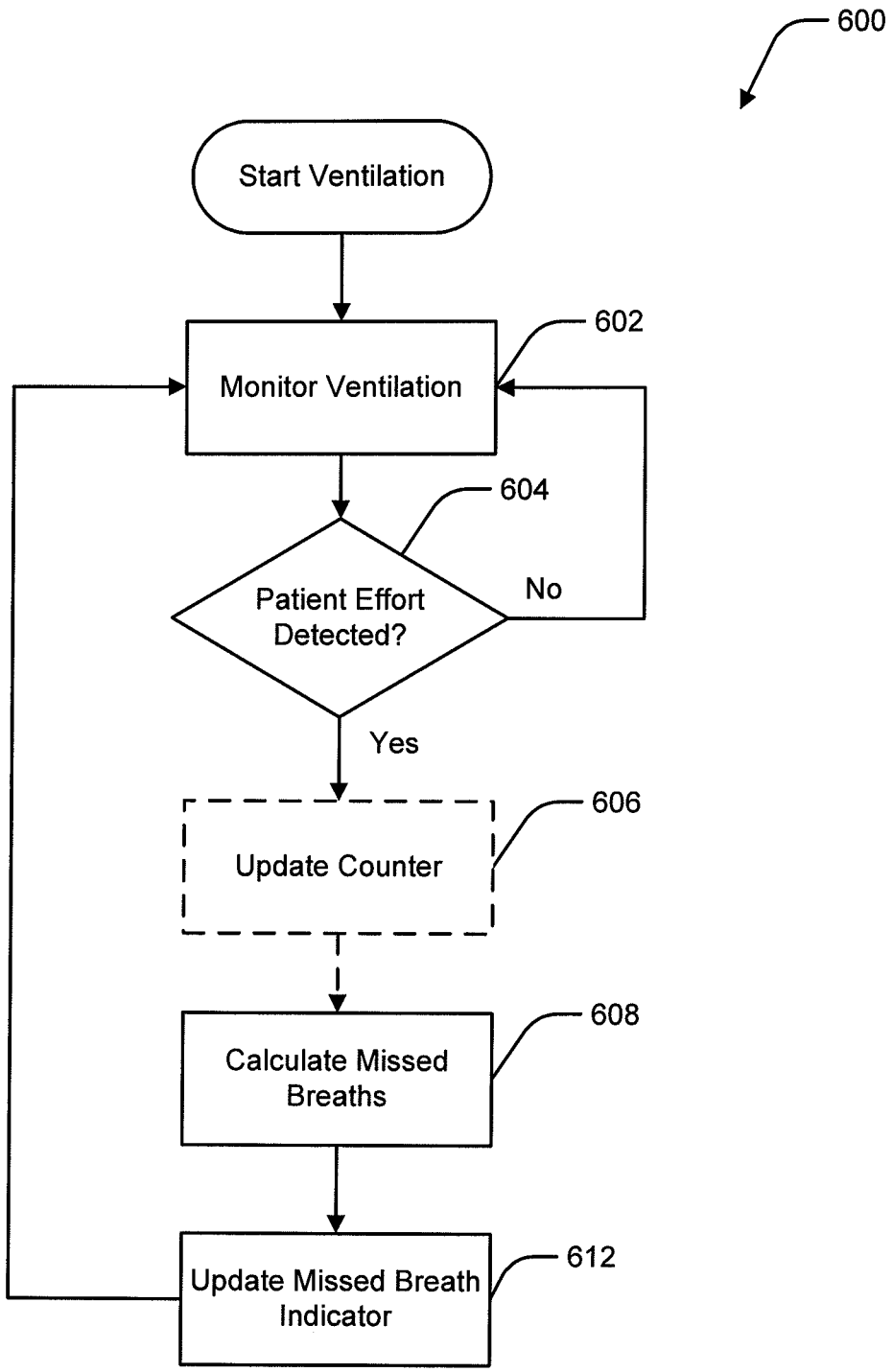
FIG. 6 is a flow diagram illustrating an embodiment of a method for displaying and/or updating the display of a missed breath indicator.

FIG. 6 is a flow diagram illustrating an embodiment of a method 600 for displaying and/or updating the display of a missed breath indicator. In an embodiment, the method 600 is performed by the missed breath module 109 described in FIG. 1. As illustrated, the ventilator system during the method 600 starts ventilation as is described with respect to starting ventilation in the above method 300. The method 600 further includes a monitor ventilation operation 602, a detect patient effort operation 604, a calculate missed breaths operation 608, and an update missed breath indicator operation 612. In an embodiment, the method further includes an update counter operation 606.

The method 600 includes the monitor ventilation operation 602. During the monitor ventilation operation 602 the ventilator monitors respiratory data with at least one sensor. In an embodiment, the at least one sensor is similar to the sensors utilized by the monitoring modules 216-222 as described above. In an embodiment, the respiratory data includes at least one of a pressure, flow, volume, intrapleural pressure, and/or any other data collected regarding the physical condition of the patient.

The method 600 further includes the detect patient effort operation 604. During the detect patient effort operation 604 the ventilator analyzes the respiratory data with a first trigger detection application and a second trigger detection application. Further, during the detect patient effort operation 604 the ventilator detects patient inspiratory and/or expiratory efforts with the first trigger detection application and the second trigger detection application. In an embodiment, the ventilator uses at least two trigger detection applications to analyze the monitored respiratory data. As discussed above, a trigger detection application is a hardware or software application that determines when a patient effort occurs based on a selected or predetermined spontaneous breath type. The second, or active trigger detection application may include Proportional Assist Ventilation (PAV), Volume Ventilation Plus (VV+), I:E SYNC, Pressure Support (PS), Volume Support (VS), Assist Control (AC), Volume Control (VC), Pressure Control (PC), Airway Pressure Release Ventilation (APRV), Continuous Positive Airway Pressure (CPAP), and BiLevel Positive Airway Pressure (BPAP). The active trigger detection application may determine patient efforts based on monitoring respiratory parameters such as but not limited to pressure and flow. In one embodiment the first, or background trigger detection application is I:E SYNC. In this embodiment, the background trigger detection application determines patient effort based on monitoring intrapleural pressure.

During the detect patient effort operation 604 if a patient effort is not detected by a trigger detection application, the method 600 will return to the monitor ventilation operation 602. During the detect patient effort operation 604 if a patient effort is detected by a trigger detection application, the method 600 will proceed to the calculate missed breaths operation 608. In an embodiment, during the detect patient effort operation 604 if a patient effort is detected by a trigger detection application, the method 600 will proceed to the update counter operation 606.

The method 600 includes the calculate missed breaths operation 608. In an embodiment, during the calculate missed breaths operation 608 the ventilator calculates a missed breaths metric based on detected patient inspiratory and/or expiratory efforts by the first trigger detection application and detected patient inspiratory and/or expiratory efforts by the second trigger detection application. A missed breaths metric is an equation, number, point in time, value, percentage, rate, ratio, relationship, or any other suitable representation of missed breaths. In an embodiment, if the first trigger detection application detects a patient inspiratory and/or expiratory effort that is not within an expected and reasonable time delay, such as 3 seconds or less, of a patient inspiratory and/or expiratory effort detected by the second trigger detection application, then a breath has been missed. The ventilator during the calculate missed breaths operation 608 may store a single instance of a missed breath or a sequential history of the missed breaths over a predetermined period of time or a period of time set by a clinician. In an embodiment, an equation or mathematical operation is used to determine if the first detected patient effort correlates with the second detected patient effort.

In an embodiment, the ventilator during the calculate missed breaths operation 608 calculates a missed breaths metric based on the at least one counter. In this embodiment, the method 600 further includes the update counter operation 606. During the update counter operation 606 the ventilator updates a counter with a sum of the detected patient inspiratory and/or expiratory efforts by the first trigger detection application and a sum of the detected patient inspiratory and/or expiratory efforts by the second trigger detection application. In an embodiment, at least two counters are used, where a first counter is updated with a sum of the detected patient inspiratory and/or expiratory efforts by the first trigger detection application and a second counter is updated with a sum of the detected patient inspiratory and/or expiratory efforts by the second trigger detection application. In an embodiment, a single counter is used where a count of patient inspiratory and/or expiratory efforts detected with the first trigger detection application is added to the counter and a count of patient inspiratory and/or expiratory efforts detected with the second trigger detection application is subtracted from the counter. In another embodiment a mathematical model, or algorithm is used to calculate how patient inspiratory and/or expiratory efforts detected with the first or second trigger detection applications update at least one counter. In an embodiment, the at least one counter is reset after a predetermined amount of time or breath cycles, or in response to clinician input.

In an embodiment, a first counter represents a sum of patient inspiratory and/or expiratory efforts detected with a first trigger detection application and a second counter represents a sum of patient inspiratory and/or expiratory efforts detected with a second trigger detection application. The ventilator during the calculate missed breaths operation 608 performs an algorithm or mathematical operation, such as subtracting the count of the second counter from the count of the first counter, with the two counters to calculate a missed breaths metric. In an embodiment, the value of a counter represents a missed breaths metric and no further algorithm or mathematical operation is needed to calculate the missed breaths metric. In another embodiment, a single counter is used and an algorithm or mathematical operation must be performed with the counter in order to calculate the missed breaths metric. Indeed, the missed breaths metric may be calculated according to any suitable method.

The method 600 further includes the update missed breath indicator operation 612. The ventilator during the update missed breath indicator operation 612 displays a missed breath indicator based on the missed breaths metric. In an embodiment, the ventilator during the update missed breath indicator operation 612 updates the display of a previously displayed missed breath indicator based on the missed breaths metric. The ventilator may store a sequential history of the missed breath indicators provided. The missed breath module 211, or another suitable component and/or module, may archive missed breath indicators according to time, and may associate a time element with the missed breath indicators. In the alternative, the monitoring modules 216-222 may associate the missed breath indicators with a time element, or time stamp, before communicating data to the graphics module 226 and/or the missed breath module 211. In either case, missed breath indicators may be archived in sequential order based on time, resulting in an archived ineffective indicator. In an embodiment, the missed breath indicator is displayed on top of a graphical representation of a respiratory signal such as, but not limited to, pressure and flow, at an appropriate temporal location based on when the missed breath occurred. In an embodiment, a missed breath is displayed as at least one of text, symbol, prompt, graphic, light, line, cursor, interactive element, indicator, or by another suitable form of graphic display.

In another embodiment the missed breath indicator displays a missed breath rate. This rate can be the number or an average of the number of missed breaths per time period, where the time period can be predetermined, such as a minute, or input by the clinician. For example, a missed breath indicator displays the number of missed breaths in the last minute. The average can be taken from a predetermined or input number of values over a predetermined or input period of time. For example, a missed breath indicator displays a rate based on an average of the last five values where each value represents the number of missed breaths for that minute. In an embodiment, a missed breath indicator displays a percentage or ratio at least partially representative of the missed breaths. For example, if the number of delivered breaths as well as the number of missed breaths are both known, then a missed breath indicator representing a percentage or ratio of missed breaths per total breaths may be displayed where total breaths is the addition of missed breaths and delivered breaths. In an embodiment, the missed breath indicator displays a total breath indicator where the total breath indicator at least partially represents the total breaths, where the total breaths is the addition of missed breaths and delivered breaths.

Additionally, a missed breath indicator may be displayed to represent that missed breaths are being monitored. Further, a missed breath indicator may be displayed to represent settings for monitoring missed breaths. For example, a missed breath indicator displays a prompt with adjustable elements representative of turning on and/or off the missed breath monitoring as well as inhalation and exhalation trigger values for missed breath monitoring using the first trigger detection application. Indeed, data may be collected and displayed according to any suitable method.

In an embodiment, the method 600 following the update missed breath indicator operation 612 returns to the monitor ventilation operation 602.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method implemented by a ventilator for determining missed breaths, the method comprising:
   monitoring, by the ventilator, respiratory data of [[the]]a patient;
   concurrently analyzing the respiratory data using a background trigger detection application and an active trigger detection application, wherein the background trigger detection application and the active trigger detection application are different;
   detecting a first patient inspiratory effort with the active trigger application;
   detecting a second patient inspiratory effort with the background trigger application;
   determining a timing difference between the first patient inspiratory effort and the second inspiratory effort;
   comparing the timing difference to a time delay threshold;
   forming a missed breath determination based on the comparison;
   calculating a missed breaths metric based on the missed breath determination;
   displaying a missed breath indicator based on the missed breaths metric; and
   delivering inspiratory gas to the patient with the ventilator based on the first patient inspiratory effort and not based on the second patient inspiratory effort.

2. The method according to claim 1, wherein the background trigger detection application monitors patient inspiratory efforts based on at least intrapleural pressure.

3. The method according to claim 1, wherein calculating the missed breaths metric comprises:
   updating a counter with a first sum of detected patient inspiratory efforts by the background trigger detection application and a second sum of detected patient inspiratory efforts by the active trigger detection application;
   determining a difference between the first sum of the detected patient inspiratory efforts and the second sum of the detected patient inspiratory efforts; and
   calculating the missed breaths metric based on the difference.

4. The method according to claim 1, wherein calculating the missed breaths metric comprises:
   updating a first counter with a first sum of detected patient inspiratory efforts by the background trigger detection application and a second counter with a second sum of detected patient inspiratory efforts by the active trigger detection application;
   determining a difference between the first counter and the second counter; and
   calculating the missed breaths metric based on the difference.

5. The method according to claim 1, wherein displaying the missed breath indicator comprises:
   generating a graphical representation of the respiratory data;
   determining a position for the missed breath indicator on the graphical representation based on a time element associated with the missed breaths metric; and
   displaying the missed breath indicator at the position on the graphical representation.

6. The method according to claim 1, wherein displaying the missed breath indicator comprises:
   archiving one or more missed breaths metrics during a time period;
   determining a missed breath indicator corresponding to the archived one or more missed breaths metrics; and
   displaying the corresponding missed breath indicator.

7. The method according to claim 6, wherein displaying the corresponding missed breath indicator comprises:
   generating a graphical representation of the respiratory data;
   determining a position for the corresponding missed breaths indicator on the graphical representation based on the time period associated with the archived one or more missed breaths metrics; and
   displaying the corresponding missed breath indicator at the position on the graphical representation.

8. A ventilator system comprising:
   a pneumatic system for delivering respiratory gases to a patient;
   at least one processor; and
   at least one memory communicatively coupled to the at least one processor and storing computer executable instructions that, when executed by the at least one processor, cause the ventilator system to perform operations comprising:
   monitoring respiratory data of the patient;
   concurrently analyzing the respiratory data using a background trigger detection application and an active trigger detection application, wherein the background trigger detection application and the active trigger detection application are different;
   detecting a first patient inspiratory effort with the active trigger application;
   detecting a second patient inspiratory effort with the background trigger application;
   determining a timing difference between the first patient inspiratory effort and the second inspiratory effort;
   comparing the timing difference to a time delay threshold;

forming a missed breath determination based on the comparison;

calculating a missed breaths metric based on the missed breath determination;

displaying a missed breath indicator based on the missed breaths metric; and delivering inspiratory gas to the patient with the ventilator based on the first patient inspiratory effort and not based on the second patient inspiratory effort.

9. The ventilator system according to claim 8, wherein the background trigger detection application monitors patient inspiratory efforts based on at least intrapleural pressure.

10. The ventilator system according to claim 8, wherein calculating the missed breaths metric comprises:

updating a counter with a first sum of detected patient inspiratory efforts by the background trigger detection application and a second sum of detected patient inspiratory efforts by the active trigger detection application;

determining a difference between the first sum of the detected patient inspiratory efforts and the second sum of the detected patient inspiratory efforts; and calculating the missed breaths metric based on the difference.

11. The ventilator system according to claim 8, wherein calculating the missed breaths metric comprises:

updating a first counter with a first sum of detected patient inspiratory efforts by the background trigger detection application and a second counter with a second sum of detected patient inspiratory efforts by the active trigger detection application;

determining a difference between the first counter and the second counter; and calculating the missed breaths metric based on the difference.

12. The ventilator system according to claim 8, wherein displaying the missed breath indicator comprises:

generating a graphical representation of the respiratory data;

determining a position for the missed breath indicator on the graphical representation based on a time element associated with the missed breaths metric; and displaying the missed breath indicator at the position on the graphical representation.

13. The ventilator system according to claim 8, wherein displaying the missed breath indicator comprises:

archiving one or more missed breaths metrics during a time period;

determining a missed breath indicator corresponding to the archived one or more missed breaths metrics; and displaying the corresponding missed breath indicator.

14. The ventilator system according to claim 13, wherein displaying the corresponding missed breath indicator comprises:

generating a graphical representation of the respiratory data;

determining a position for the corresponding missed breaths indicator on the graphical representation based on the time period associated with the archived one or more missed breaths metrics; and displaying the corresponding missed breath indicator at the position on the graphical representation.

* * * * *